(12) United States Patent
Lubbe

(10) Patent No.: US 12,172,373 B2
(45) Date of Patent: Dec. 24, 2024

(54) DEVICES, SYSTEMS, AND METHODS FOR 3D PRINTING

(71) Applicant: Steven Lubbe, Epping, NH (US)

(72) Inventor: Steven Lubbe, Epping, NH (US)

( * ) Notice: Subject to any disclaimer, the term of this patent is extended or adjusted under 35 U.S.C. 154(b) by 429 days.

(21) Appl. No.: 17/292,313

(22) PCT Filed: Nov. 25, 2020

(86) PCT No.: PCT/US2020/062327
§ 371 (c)(1),
(2) Date: May 7, 2021

(87) PCT Pub. No.: WO2021/108634
PCT Pub. Date: Jun. 3, 2021

(65) Prior Publication Data
US 2023/0133547 A1 May 4, 2023

Related U.S. Application Data

(60) Provisional application No. 63/083,477, filed on Sep. 25, 2020, provisional application No. 62/940,560, filed on Nov. 26, 2019.

(51) Int. Cl.
*B29C 64/165* (2017.01)
*B29C 64/188* (2017.01)
(Continued)

(52) U.S. Cl.
CPC .......... *B29C 64/165* (2017.08); *B29C 64/188* (2017.08); *B29C 64/227* (2017.08); *B29C 64/255* (2017.08); *B29C 64/264* (2017.08); *B29C 64/268* (2017.08); *B29C 64/277* (2017.08); *B29C 64/286* (2017.08); *B29C 64/364* (2017.08); *B29C 64/393* (2017.08);
(Continued)

(58) Field of Classification Search
CPC ... B29C 64/165; B29C 64/124; B29C 64/129; B29C 64/135
See application file for complete search history.

(56) References Cited

U.S. PATENT DOCUMENTS 6,573,026 B1 6/2003 Aitken et al.
6,585,875 B1 7/2003 Ryabkov
(Continued)

FOREIGN PATENT DOCUMENTS

CA 2977288 A1 9/2016
CN 101449295 B 6/2012
(Continued)

OTHER PUBLICATIONS

Elomaa et al., "Three-dimensional fabrication of cell-laden biodegradable poly(ethylene glycol-co-depsipeptide) hydrogels by visible light stereolithography", J. Mater. Chem. B, 2015, 3, 8348-8358. (Year: 2015).*

(Continued)

*Primary Examiner* — Atul P. Khare
(74) *Attorney, Agent, or Firm* — Clark & Elbing LLP

(57) ABSTRACT

The invention provides devices, systems, and methods for 3D printing. The invention employs slurries of particles or a solute in a carrier fluid, which may be a liquid or gas, in printing. The use of a slurry is advantageous in allowing for printing in any orientation.

18 Claims, 17 Drawing Sheets

(51) Int. Cl.

| | |
|---|---|
| B29C 64/227 | (2017.01) |
| B29C 64/255 | (2017.01) |
| B29C 64/264 | (2017.01) |
| B29C 64/268 | (2017.01) |
| B29C 64/277 | (2017.01) |
| B29C 64/286 | (2017.01) |
| B29C 64/364 | (2017.01) |
| B29C 64/393 | (2017.01) |
| B33Y 10/00 | (2015.01) |
| B33Y 30/00 | (2015.01) |
| B33Y 40/20 | (2020.01) |
| B33Y 50/02 | (2015.01) |
| B33Y 70/10 | (2020.01) |

(52) U.S. Cl.
CPC ............. *B33Y 10/00* (2014.12); *B33Y 30/00* (2014.12); *B33Y 40/20* (2020.01); *B33Y 50/02* (2014.12); *B33Y 70/10* (2020.01)

(56) References Cited

U.S. PATENT DOCUMENTS

| | | | |
|---|---|---|---|
| 6,597,388 B2 | 7/2003 | Pierson | |
| 7,108,733 B2 | 9/2006 | Enokido | |
| 8,168,541 B2 | 5/2012 | Fukasawa et al. | |
| 8,270,788 B2 | 9/2012 | Herman et al. | |
| 9,446,475 B2 | 9/2016 | Norfolk et al. | |
| 9,453,289 B2 * | 9/2016 | Rose | C04B 37/025 |
| 9,656,344 B2 | 5/2017 | Kironn et al. | |
| 9,840,045 B2 * | 12/2017 | Linnell | B33Y 30/00 |
| 9,952,448 B2 * | 4/2018 | Crespo Vázquez | B29D 11/00442 |
| 9,956,640 B2 | 5/2018 | Burke et al. | |
| 10,118,343 B1 * | 11/2018 | Linnell | B29C 64/245 |
| 10,228,617 B2 * | 3/2019 | Gates | G02B 7/02 |
| 10,792,859 B2 * | 10/2020 | Van Esbroeck | B33Y 30/00 |
| 10,814,546 B2 * | 10/2020 | Chen | B29C 64/135 |
| 10,836,105 B2 * | 11/2020 | Houbertz | B33Y 70/00 |
| 11,654,618 B2 * | 5/2023 | Pingel | B29C 64/236 264/401 |
| 2006/0118990 A1 * | 6/2006 | Dierkes | A61C 13/001 264/105 |
| 2006/0156978 A1 | 7/2006 | Lipson et al. | |
| 2007/0279467 A1 | 12/2007 | Regan et al. | |
| 2010/0266087 A1 | 10/2010 | Ahlfeld et al. | |
| 2012/0145681 A1 | 6/2012 | Fujiuchi et al. | |
| 2014/0093699 A1 | 4/2014 | Xu | |
| 2016/0193688 A1 | 7/2016 | Kironn et al. | |
| 2016/0234970 A1 | 8/2016 | Shelnutt et al. | |
| 2016/0236372 A1 | 8/2016 | Benichou et al. | |
| 2016/0263827 A1 | 9/2016 | Fripp et al. | |
| 2016/0288207 A1 | 10/2016 | Gambardella | |
| 2017/0242424 A1 | 8/2017 | Spears | |
| 2018/0178314 A1 | 6/2018 | MacCormack et al. | |
| 2018/0185955 A1 | 7/2018 | Hsu et al. | |
| 2018/0265998 A1 * | 9/2018 | Mora | C25D 5/022 |
| 2018/0304539 A1 | 10/2018 | Ng et al. | |
| 2018/0369912 A1 * | 12/2018 | Gold | B33Y 40/00 |
| 2019/0048486 A1 | 2/2019 | Voros et al. | |

FOREIGN PATENT DOCUMENTS

| | | | | |
|---|---|---|---|---|
| CN | 208216019 U | * | 12/2018 | |
| CN | 109760301 A | * | 5/2019 | |
| CN | 111347038 A | * | 6/2020 | |
| DE | 102019121106 A1 | * | 11/2020 | B29C 64/135 |
| EP | 2318137 B1 | | 9/2018 | |
| WO | WO-2015/191257 A1 | | 12/2015 | |
| WO | WO-2016/008464 A1 | | 1/2016 | |
| WO | WO-2019219916 A2 | * | 11/2019 | A61L 24/001 |

OTHER PUBLICATIONS

Boccaccini et al., "Electrophoretic deposition of biomaterials", J. R. Soc. Interface (2010) 7, S581-S613. (Year: 2010).*

Amrollahi et al., "Electrophoretic Deposition (EPD): Fundamentals and Applications from Nano- to Micro-Scale Structures", Handbook of Nanoelectrochemistry, Jun. 2015, 1-27. (Year: 2015).*

Han et al., "Electrophoretic Deposition of Gentamicin-Loaded Silk Fibroin Coatings on 3D-Printed Porous Cobalt-Chromium-Molybdenum Bone Substitutes to Prevent Orthopedic Implant Infections", Biomacromolecules 18(11), 2017, pp. A-L. (Year: 2017).*

Vogt et al., "Usability of electrophoretic deposition for additive manufacturing of ceramics", Ceramics International 45 (2019) 14214-14222. (Year: 2019).*

"Technology," 3D Micro Print, <https://www.3dmicroprint.com/technology>, Sep. 2, 2019 (3 pages) retrieved from Internet Archive Wayback Machine <https://web.archive.org/web/20190902204829/https://www.3dmicroprint.com/technology> Sep. 2, 2019.

Deckers et al., "Additive Manufacturing of Ceramics: A Review," J Ceram Sci tech. 5(4):245-260 (Nov. 3, 2014).

Digital Alloys, <https://www.digitalalloys.com>, Apr. 3, 2019 (4 pages) retrieved from Internet Archive Wayback Machine <https://web.archive.org/web/20190403150418/https://www.digitalalloys.com/> as available on Apr. 3, 2019.

Essop, Anas, "Tu Graz Engineers Create Metal 3D Printer that Uses LED Instead of Lasers or Electron Beams," 3D Printing Industry, <https://3dprintingindustry.com/news/tu-graz-engineers-create-metal-3d-printer-that-uses-led-instead-of-lasers-or-electron-beams-171609/>, published May 12, 2020 (6 pages) retrieved from Internet Archive Wayback Machine <https://web.archive.org/web/20200801000000*/https://3dprintingindustry.com/news/tu-graz-engineers-create-metal-3d-printer-that-uses-led-instead-of-lasers-or-electron-beams-171609> as available on Jun. 6, 2020.

Foresti et al., "Acoustophoretic printing," Sci Adv. 4(8):eaat1659 (Aug. 31, 2018) (9 pages).

Hu et al., "UV-Resistant Self-Healing Emulsion Glass as a New Liquid-like Solid Material for 3D Printing," ACS Appl Mater Interfaces. 12(21):24450-24457 (May 15, 2020).

Huang, Stefan, "The Basics of Ultrasonic Plastic Welding Technology," NexPCB, <https://www.nexpcb.com/blog/the-basics-of-ultrasonic-welding-technology>, published on May 10, 2018 (6 pages) retrieved from Internet Archive Wayback Machine <https://web.archive.org/web/20200808063405/https://www.nexpcb.com/blog/the-basics-of-ultrasonic-welding-technology> as available on Aug. 8, 2020.

International Search Report and Written Opinion for International Patent Application No. PCT/US2020/062327, mailed Mar. 26, 2021 (34 pages).

J., Michelle, "Researchers develop 3D printing with sound waves," 3Dnatives, <https://www.3dnatives.com/en/researchers-3d-printing-sound-waves-291120185/#!>, published on Nov. 29, 2018 (8 pages).

LeBlanc et al., "Stability of high speed 3D printing in liquid-like solids." ACS Biomaterials Science & Engineering. 2(10): 1796-1799 (Aug. 17, 2016).

Ren et al., "3D gel-printing—An additive manufacturing method for producing complex shape parts," Mat Design. 101:80-87 (Apr. 5, 2016).

Scott, Claire, "XJet to Showcase Nanoparticle Jetting Metal 3D Printing Technology at formnext," 3DPrint.com, published on Nov. 1, 2016 (4 pages) retrieved from Internet Archive Wayback Machine <https://web.archive.org/web/20201024025435/https://www.3dprint.com/154070/xjet-nanoparticle-jetting-formnext/> as available on Oct. 24, 2020.

Singh et al., "The adoption of three-dimensional additive manufacturing from biomedical material design to 3d organ printing." Applied Sciences. 9(4): 811 (Feb. 25, 2019) (13 pages).

"Agitator," Merriam-Webster, <https://web.archive.org/web/20191001122731/https://www.merriam-webster.com/dictionary/agitator>, captured on Oct. 10, 2019 (1 page).

Benkreira, H., "Mixing," Thermopedia, dated Feb. 2, 2011, last modified Feb. 14, 2011, retrieved from <https://www.thermopedia.com/content/960/> on Oct. 25, 2023 (9 pages).

* cited by examiner

Fig. 1
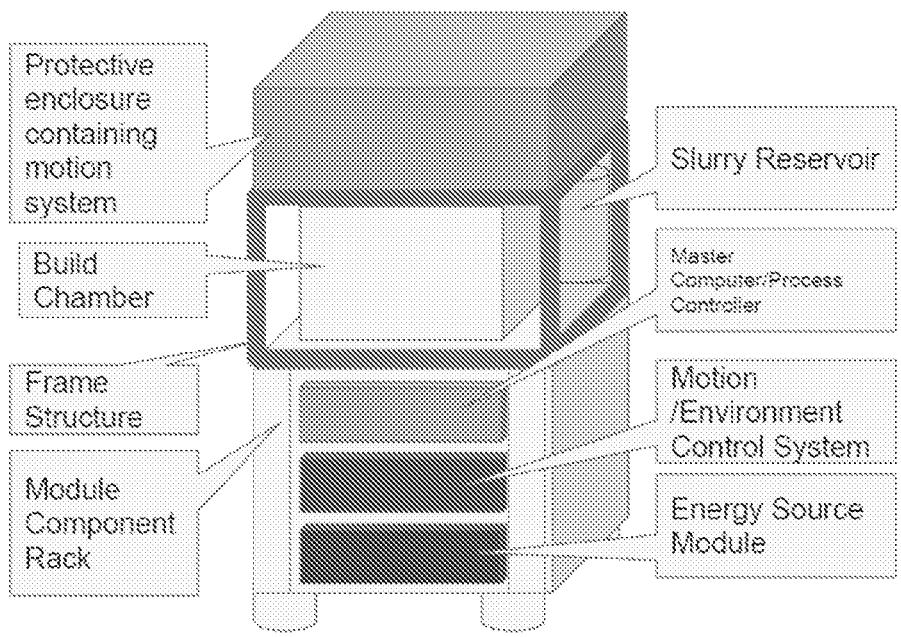
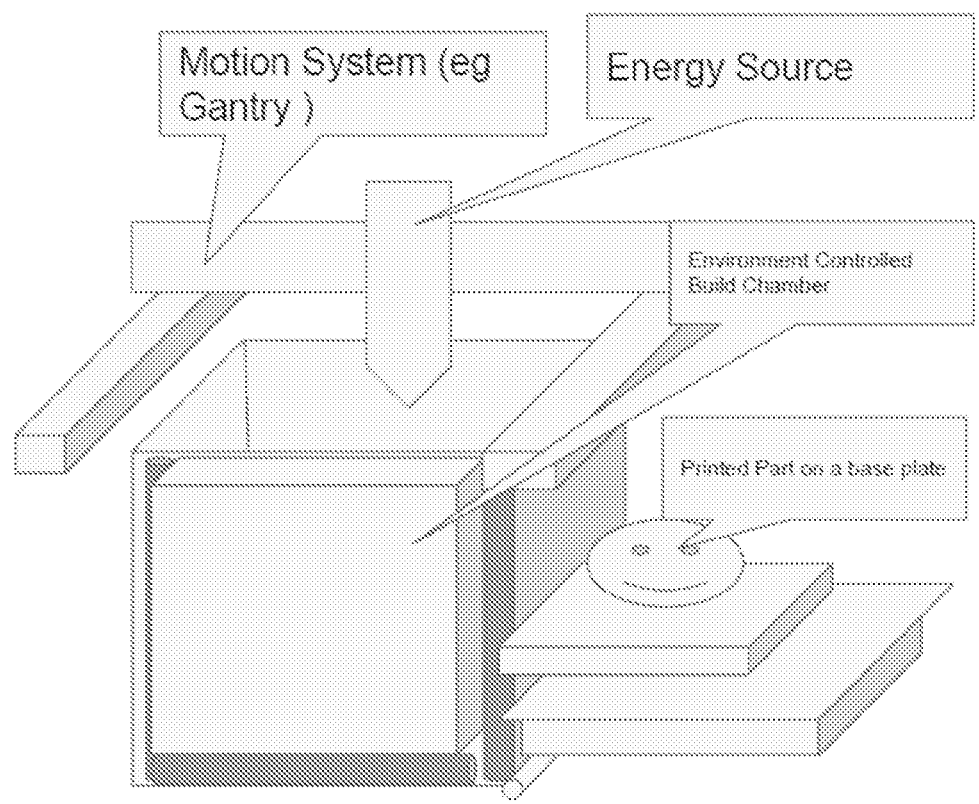
Fig. 2

Fig. 3
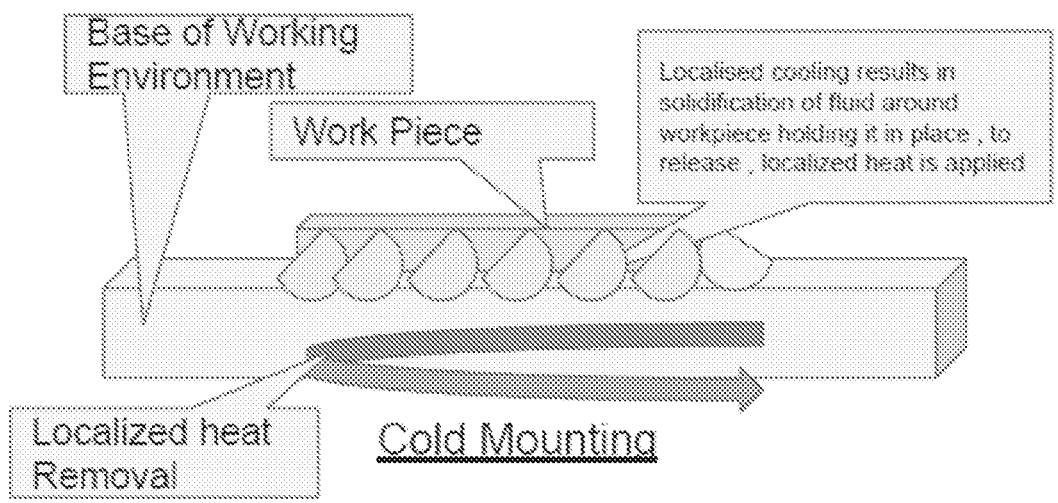
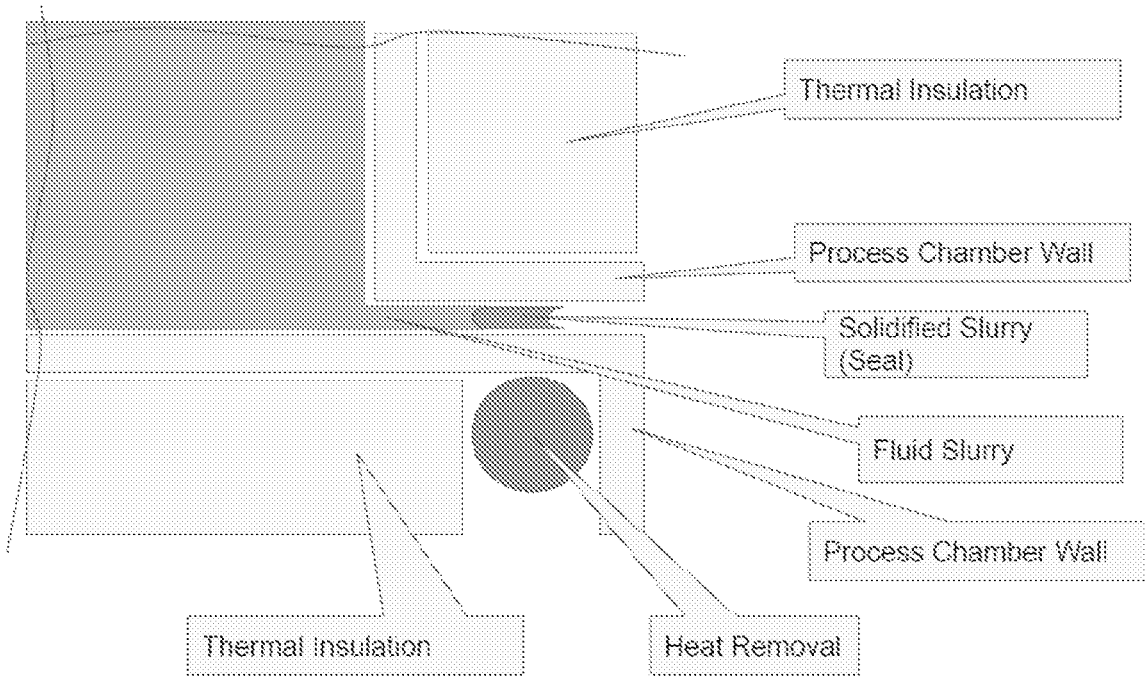
Fig. 4

Fig. 5
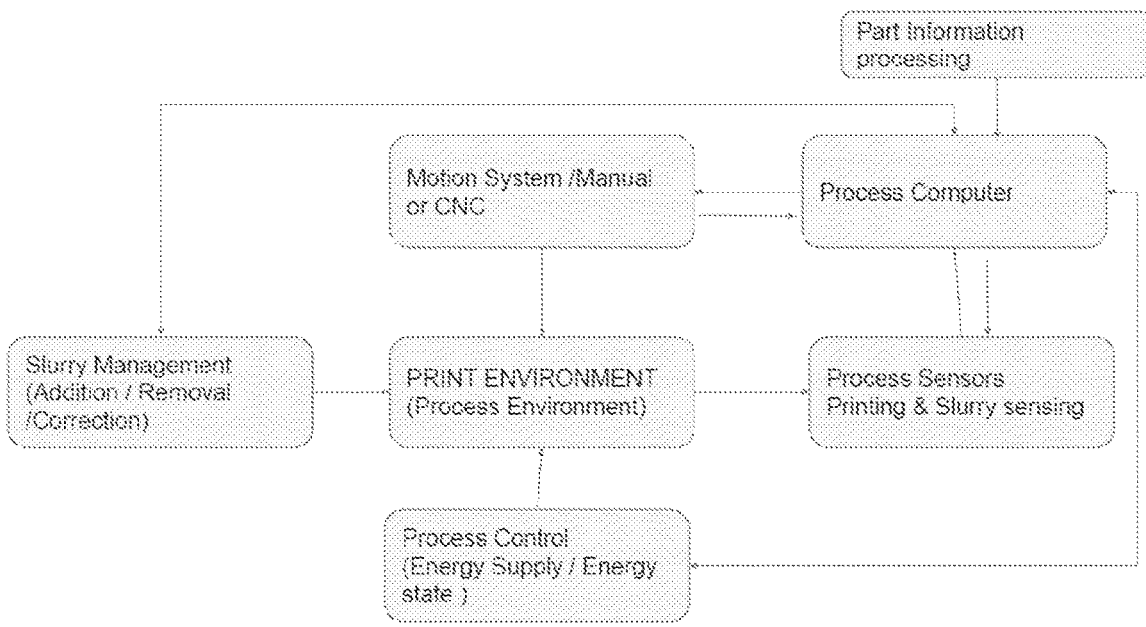
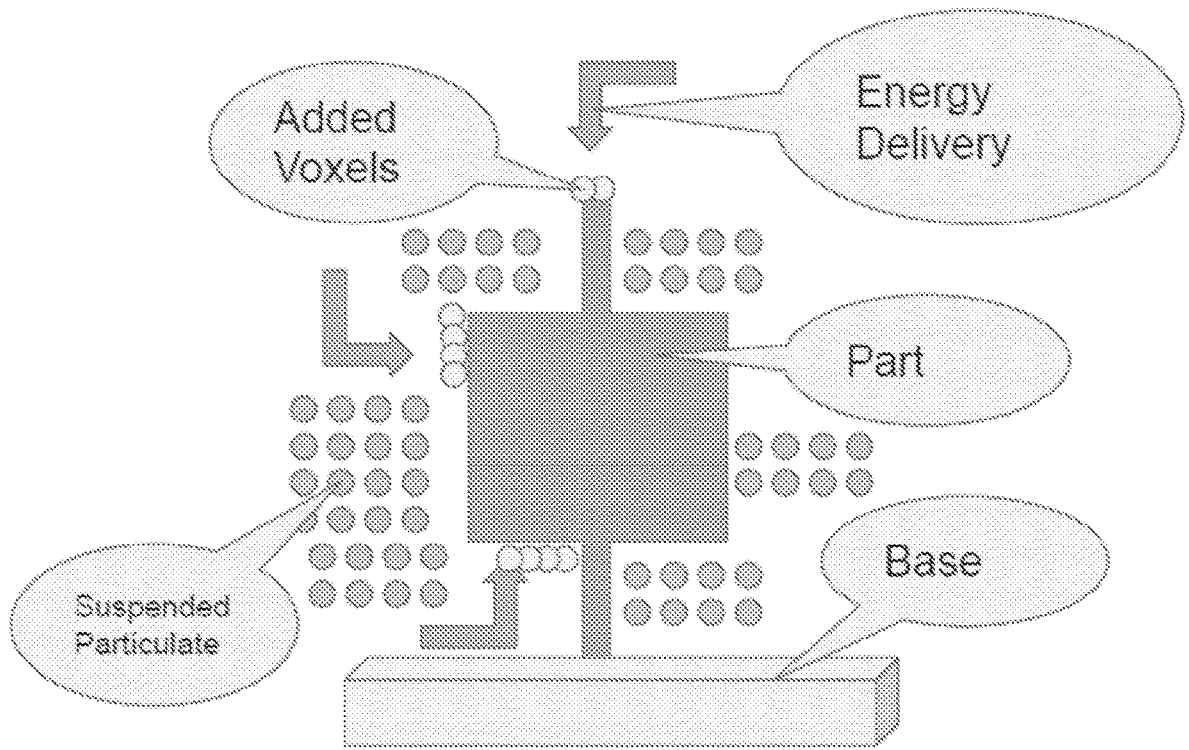
Fig. 6

Fig. 7
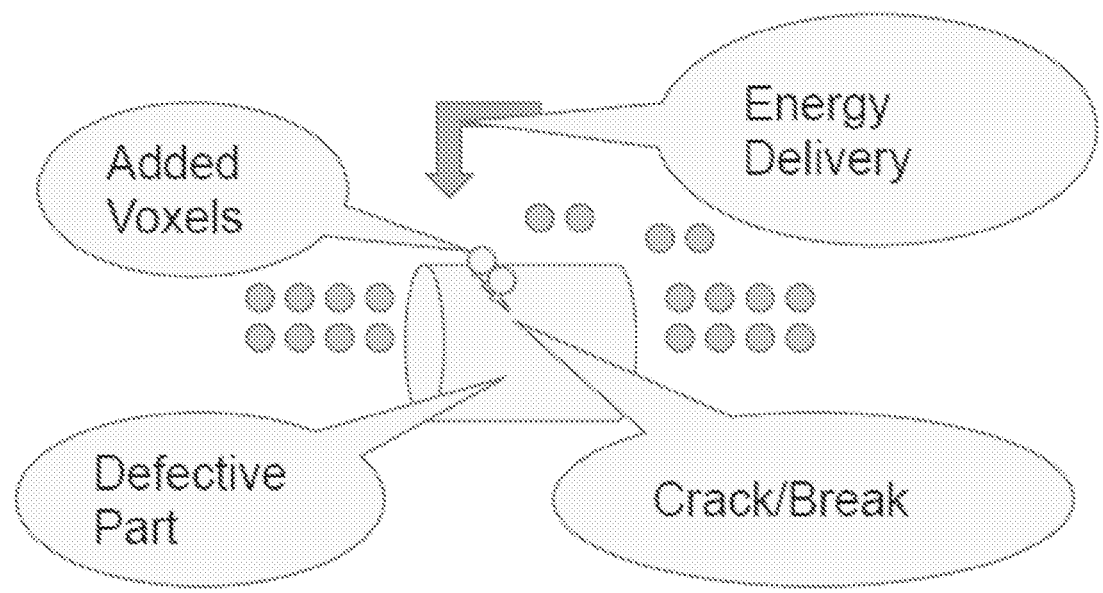
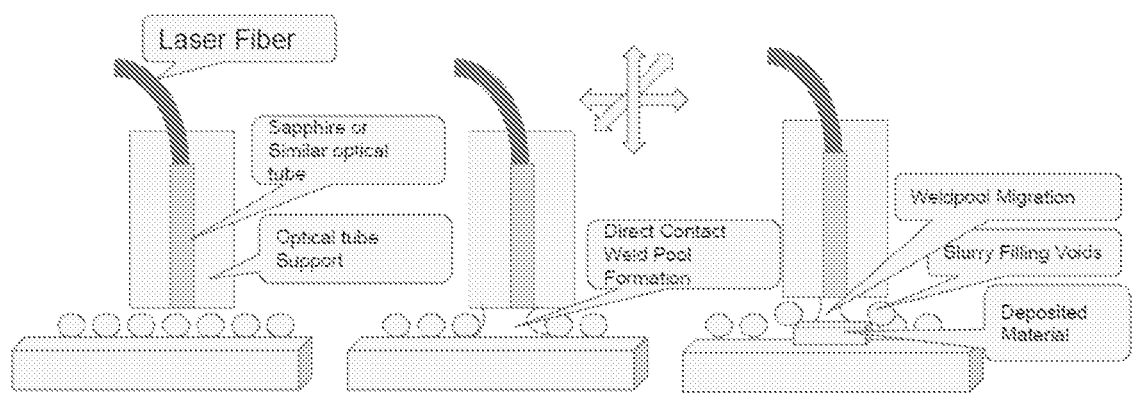
Fig. 8

DEVICES, SYSTEMS, AND METHODS FOR 3D PRINTING

BACKGROUND OF THE INVENTION

The 3D printing toolbox of technologies includes two predominant method types: a continuous method, in which material is continuously deposited (such as fused deposition modeling (FDM) or Direct Energy Deposition (DED)) and an intermittent method in which a layer is intermittently processed and recoated layer by layer (such as selective laser melting (SLM) and Binder Jet printing). Each process differs in speed, scale (size), and/or accuracy (repeatability, detail).

For example, SLM processes allow for high density metal parts to be made in high detail, but at low speeds and with the aid of support structures that allow for geometric repeatability. Material in a powder format is usually chosen as the process media. Powder which when stationary and made to the desired characteristics allows for accurate weld pools to be formed, and the size of which along with energy delivery dictates the detail to which parts can be printed. The energy density is also a limiting factor as the media could be pushed away by rapidly expanding gases, resulting in process defects or irregularities.

Continuous 3D printing methods allow for great speed and size but lack detail as material that is solid needs to be made molten or liquid to be continuously deposited. Other continuous methods take powder media and blast it at a weld pool so as to avoid using solid media. Due to the variability in how material is deposited, the process results in lower detail or repeatability as compared to intermittent processes.

For both processes, energy delivery and media may present challenges. For example, aluminum and titanium alloys in a powder format may be pyrophoric, and media less than 10 µm in size may be dangerous to a person's health. To mitigate the compounding risk attributed to powder media, more auxiliary hardware is needed to manage and handle the printing media, resulting in the need for more equipment. Power delivery systems, which most often consist of inefficient laser delivery, require costly delivery control systems which add to the overall cost of the system. For certain processes, printing the final part is not the last step as the part would need to go through various post processing in order for it to have the desired metallurgical composition or physical properties. Again, more auxiliary equipment is needed.

Process environmental control is of absolute importance as some materials have a high affinity for impurities, such as oxygen and nitrogen, and other media require the right moisture-gas composition in order to maintain a repeatable process.

Accordingly, there is a need for new devices, systems, and methods for 3D printing.

SUMMARY OF THE INVENTION

In one aspect, the invention provides a device for printing including a build chamber capable of holding a slurry; an energy source; and a base. At least one of the energy source and the base is coupled to a motion system to allow relative movement of the energy source with respect to the base in the build chamber.

In embodiments, the energy source includes one or more electrodes; a plasma source; a fissile or radioactive energy source; a particle beam source; a microwave source; a resistive heating source; a kinetic energy source; a friction source; a light source; an RF (Radio Frequency) source; an acoustic or ultrasonic source; a direct heat source; an organic stimuli energy source; a catalytic energy source; a magnetic energy source; an osmosis energy source; or a combination thereof. In embodiments, the slurry includes a carrier fluid that is a liquid. Alternatively, the slurry includes a carrier fluid that is a gas. In embodiments, the device further includes a reservoir for the slurry. In embodiments, the energy source comprises a deposition point and a lumen disposed to deliver slurry to the deposition point. In embodiments, the device further includes an agitator or mixer operably connected to the build chamber and/or a temperature, pressure, or humidity controller. In embodiments, the energy source includes a laser and an optical tube, and light from the laser exits via the optical tube and melts particles in the slurry to provide a weld pool. The device may further include a probe positionable to contact the weld pool.

In embodiments, the light source includes a UV light and/or one or more LEDs, where each LED has an efficiency of at least 40 lm/W. In embodiments, the device further includes a second lumen disposed to remove excess slurry from the deposition point. In embodiments, the one or more electrodes includes an arc electrode. In embodiments, the slurry includes conductive particles in a dielectric liquid. In embodiments, the slurry includes a liquid like solid emulsion. In embodiments, the one or more electrodes includes first and second electrodes, where the second electrode is configured to direct a flow of current between the first electrode and the base and/or to provide a source of sacrificial ions. In embodiments, the lumen is configured to be re-sizeable or replaceable during printing. In embodiments, the device further includes a plurality of energy sources configured to be changed during printing. In embodiments, the energy source includes a two-dimensional or three-dimensional matrix including a plurality of light sources. In embodiments, the slurry includes biological particles and the energy source is configured to stimulate deposition of the biological particles by selective scarring or fibrosis. In embodiments, the magnetic energy source is configured to direct particles or solute to the base for deposition by another energy source. In embodiments, the slurry includes two or more materials that fuse. In embodiments, the energy source includes a deposition point and a lumen disposed to deliver a gas flow to the deposition point. In embodiments, the energy source includes a non-conductive shroud around the deposition point. In embodiments, the gas flow is configured to protect the deposition point and/or to shape the slurry at the deposition point. In embodiments, the gas flow is configured to create an optically transparent low friction interface between the base and/or slurry and the energy source. In embodiments, the energy source includes a deposition point including a seeding sample of one or more of the particles or solutes in the slurry. In embodiments, the deposition point includes a material with higher electrical and/or thermal conductivity than the slurry. In embodiments, the energy source includes a sacrificial material configured to provide ions to the slurry. In embodiments, the slurry includes both particles and a solute and the particles are configured to deposit when the solute is deposited. In embodiments, the solute includes a UV-curable resin. In embodiments, the slurry includes a solute configured to produce particles. In embodiments, the build chamber includes a movable bath for the slurry and the energy source, where the base is held above the bath, and the bath and base are movable relative to each other. In embodiments, the energy source includes a light source with a mask layer. In embodiments, the slurry includes an abrasive. In embodiments, the energy source includes a fissile material and one or more fission modulating control rods. In embodiments, the energy source comprises a deposition point in which the fissile material and control rods are disposed and wherein the deposition point comprises a cover configured to withstand heat and radiation while transmitting heat to the slurry.

Another aspect of the invention provides a device for printing including an energy source; a continuously movable base; and a slurry source positioned to deliver a slurry including particles or a solute in a carrier fluid to the base.

In embodiments, the continuously movable base is configured to have adjustable speed during printing. In embodiments, the inlet is configured to provide the slurry at a rate that is pre-determined and/or the rate is adjustable during printing. In embodiments, the device further includes an outlet for recovery and recycling of excess slurry. In embodiments, the energy source is movable during printing.

In an aspect, the invention provides a system for printing including a build chamber capable of holding a slurry; an energy source; a base; and a slurry including particles or a solute in a carrier fluid. At least one of the energy source and the base is coupled to a motion system to allow relative movement of the energy source with respect to the base in the build chamber. The actuation of the energy source results in deposition of the particles or a solute to produce a printed object.

In embodiments, the energy source includes one or more electrodes; a plasma source; a fissile or radioactive energy source; a particle beam source; a microwave source; a resistive heating source; a kinetic energy source; a friction source; a light source; an RF (Radio Frequency) source; an acoustic or ultrasonic source; a direct heat source; an organic stimuli energy source; a catalytic energy source; a magnetic energy source; an osmosis energy source; or a combination thereof. In embodiments, the slurry includes a carrier fluid that is a liquid. Alternatively, the slurry includes a carrier fluid that is a gas. In embodiments, the system further includes a reservoir for the slurry. In embodiments, the energy source includes a deposition point and a lumen disposed to deliver slurry to the deposition point. In embodiments, the system further includes an agitator or mixer operably connected to the build chamber and/or a temperature, pressure, or humidity controller. In embodiments, the particles include metal, polymer, glass, or biological material. In embodiments, the energy source includes a laser and an optical tube, and light from the laser exits via the optical tube and melts particles in the slurry to provide a weld pool. The system may further include a probe positionable to contact the weld pool.

In embodiments, the light source includes a UV light and/or one or more LEDs, where each LED has an efficiency of at least 40 lm/W. In embodiments, the device of the system further includes a second lumen disposed to remove excess slurry from the deposition point. In embodiments, the one or more electrodes includes an arc electrode. In embodiments, the slurry includes conductive particles in a dielectric liquid. In embodiments, the slurry includes a liquid like solid emulsion. In embodiments, the one or more electrodes includes first and second electrodes, where the second electrode is configured to direct a flow of current between the first electrode and the base and/or to provide a source of sacrificial ions. In embodiments, the lumen is configured to be re-sizeable or replaceable during printing. In embodiments, the device of the system further includes a plurality of energy sources configured to be changed during printing. In embodiments, the energy source includes a two-dimensional or three-dimensional matrix including a plurality of light sources. In embodiments, the slurry includes biological particles and the energy source is configured to stimulate deposition of the biological particles by selective scarring or fibrosis. In embodiments, the magnetic energy source is configured to direct particles or a solute to the base for deposition by another energy source. In embodiments, the slurry includes two or more materials that fuse. In embodiments, the energy source includes a deposition point and a lumen disposed to deliver a gas flow to the deposition point. In embodiments, the energy source includes a non-conductive shroud around the deposition point. In embodiments, the gas flow is configured to protect the deposition point and/or to shape the slurry at the deposition point. In embodiments, the gas flow is configured to create an optically transparent low friction interface between the base and/or slurry and the energy source. In embodiments, the energy source includes a deposition point including a seeding sample of one or more of the particles or solutes in the slurry. In embodiments, the deposition point includes a material with higher electrical and/or thermal conductivity than the slurry. In embodiments, the energy source includes a sacrificial material configured to provide ions to the slurry. In embodiments, the slurry includes both particles and a solute and the particles are configured to deposit when the solute is deposited. In embodiments, the solute includes a UV-curable resin. In embodiments, the slurry includes a solute configured to produce particles. In embodiments, the build chamber includes a movable bath for the slurry and the energy source, where the base is held above the bath, and the bath and base are movable relative to each other. In embodiments, the energy source includes a light source with a mask layer. In embodiments, the slurry includes an abrasive. In embodiments, the energy source includes a fissile material and one or more fission modulating control rods. In embodiments, the energy source comprises a deposition point in which the fissile material and control rods are disposed and wherein the deposition point comprises a cover configured to withstand heat and radiation while transmitting heat to the slurry.

Another aspect of the invention provides a system for printing including (a) an energy source, (b) a continuously movable base, (c) a slurry including particles or a solute in a carrier fluid; and (d) a slurry source positioned to deliver the slurry to the base.

In embodiments, the continuously movable base is configured to have adjustable speed during printing. In embodiments, the inlet is configured to provide the slurry at a rate that is pre-determined and/or the rate is adjustable during printing. In embodiments, the system further includes an outlet for recovery and recycling of excess slurry. In embodiments, the energy source is movable during printing.

In an aspect, the invention provides a method for printing by providing a printer including a build chamber capable of holding a slurry; an energy source; a base; and a slurry including particles or a solute in a carrier fluid disposed in the build chamber so that the energy source is located in the slurry; positioning the energy source relative to the base at a desired location in the build chamber; and actuating the energy source to deposit particles or a solute on the base or an object coupled to the base to produce a printed object.

In embodiments, the particles or solute are evenly suspended or dissolved in the slurry. In embodiments, the carrier fluid is a liquid. Alternatively, the carrier fluid is a gas. In embodiments, the slurry contains particles that settle within the slurry to create a boundary layer with the carrier fluid. In embodiments, the energy source includes one or more electrodes; a plasma source; a fissile or radioactive energy source; a particle beam source; a microwave source; a resistive heating source; a kinetic energy source; a friction source; a light source; an RF (Radio Frequency) source; an acoustic or ultrasonic source; a direct heat source; an organic stimuli energy source; a catalytic energy source; a magnetic energy source; an osmosis energy source; or a combination thereof. In embodiments, the energy source includes a deposition point and a lumen disposed to deliver slurry to the deposition point. In embodiments, the particles include metal, polymer, glass, or biological material. In embodiments, the energy source includes a laser and an optical tube, and light from the laser exits via the optical tube and melts particles in the slurry to provide a weld pool.

In embodiments, the energy source further includes a second lumen disposed to remove excess slurry from the deposition point. In embodiments, the one or more electrodes include an arc electrode. In embodiments, the slurry includes conductive particles in a dielectric liquid. In embodiments, actuating the energy source in step (c) occurs at a voltage insufficient for breakdown of the dielectric liquid in the absence of the conductive particles. In embodiments, the energy source comprises an electrode, the electrode includes a metal, and the method further includes supplying a voltage sufficient to cause ions of the metal to electroplate the printed object. In embodiments, the slurry includes a liquid like solid emulsion. In embodiments, the one or more electrodes includes first and second electrodes, where the second electrode directs a flow of current between the first electrode and the base and/or provides a source of sacrificial ions. In embodiments, the lumen is re-sizeable or replaceable during printing. In embodiments, the energy source can be changed during printing. In embodiments, the energy source includes a two-dimensional or three-dimensional matrix including a plurality of light sources. In embodiments, the slurry includes biological particles and actuating the energy source stimulates deposition of the biological particles by selective scarring or fibrosis. In embodiments, the method further includes (d) removing the slurry; and (e) sintering the printed object. In embodiments, the magnetic energy source directs particles or a solute to the base for deposition by another energy source. In embodiments, the slurry includes two or more materials that fuse. In embodiments, the energy source includes a deposition point and a lumen disposed to deliver a gas flow to the deposition point. In embodiments, the energy source includes a non-conductive shroud around the deposition point. In embodiments, the gas flow is configured to protect the deposition point and/or to shape the slurry at the deposition point during step (c). In embodiments, the gas flow creates an optically transparent low friction interface with the base and slurry. In embodiments, the energy source includes a deposition point including a seeding sample of one or more of the particles or solutes in the slurry. In embodiments, the deposition point includes a material with higher electrical and/or thermal conductivity than the slurry. In embodiments, a sacrificial material provides ions to the slurry in step (c). In embodiments, the slurry includes both particles and a solute and deposition of the solute results in deposition of the particles. In embodiments, the solute includes a UV-curable resin. In embodiments, step (c) includes providing additives to the slurry during deposition. In embodiments, the energy source is used a first time to create a slurry from solutes, then a second time deposit the slurry. In embodiments, the build chamber includes a bath for the slurry and the energy source, the base is held above the bath, and the bath and base are movable relative to each other. In embodiments, the energy source includes a light source with a mask layer. In embodiments, the method further includes (d) removing the slurry; and (e) using the energy source or a second energy source to remove deposited particles or solute from the printed object. In embodiments, the method further includes (d) polishing the printed object. In embodiments, step (d) includes adding an abrasive to the slurry. In embodiments, polishing may be performed using the energy source. In embodiments, the energy source causes particles to deposit by resistive heating in step (c). In embodiments, the slurry may include mineral ore, interplanetary dust, regolith, mining tailings, and/or slag. In embodiments, the energy source comprises a fissile material and one or more fission modulating control rods. In embodiments, the energy source includes a deposition point in which the fissile material and control rods are disposed and wherein the deposition point comprises a cover which transmits heat from the fissile material to the slurry.

In embodiments, the method includes melting particles in the slurry with the energy source to form a weld pool, e.g., in contact with the energy source or probe and the base or the object coupled to the base, and manipulating the weld pool, e.g., by re-positioning the energy source or probe while maintaining contact with the weld pool.

Another aspect of the invention provides a method for printing including (a) providing a printer including; an energy source; a continuously movable base; a slurry source positioned to deliver a slurry including particles or a solute in a carrier fluid to the base; (b) providing the slurry to the continuously movable base and positioning the energy source relative to the continuously movable base at a desired location; and (c) actuating the energy source to deposit particles or a solute on the continuously movable base or an object coupled to the base.

In embodiments, the speed of the continuously movable base is adjusted during printing. In embodiments, the energy source is re-positioned relative to the continuously movable base during printing. In embodiments, the slurry is provided at a rate that is pre-determined and/or the rate is adjusted during printing. In embodiments, excess slurry is recovered and recycled. In embodiments, the method includes melting particles in the slurry with the energy source to form a weld pool, e.g., in contact with the energy source or probe and the continuously movable base or the object coupled to the base. In embodiments, the method further includes manipulating the weld pool, e.g., by moving the energy source or probe while maintaining contact with the weld pool.

By "slurry" is meant a mixture or solution of printable particles or a solute in a carrier fluid.

BRIEF DESCRIPTION OF THE DRAWINGS

FIG. 1 is a scheme of a printer of the invention.

FIG. 2 is a scheme of the motion system for a printer of the invention.

FIG. 3 is a scheme of cold mounting of an object to a base.

FIG. 4 is a scheme of the use of solidified slurry to retain slurry in the build chamber.

FIG. 5 is a diagram of process control for a printer of the invention.

FIG. 6 is a diagram of printing an object.

FIG. 7 is a diagram of repairing an object.

FIG. 8 is a diagram of an energy source for a printer.

DETAILED DESCRIPTION OF THE INVENTION

Figure 9:
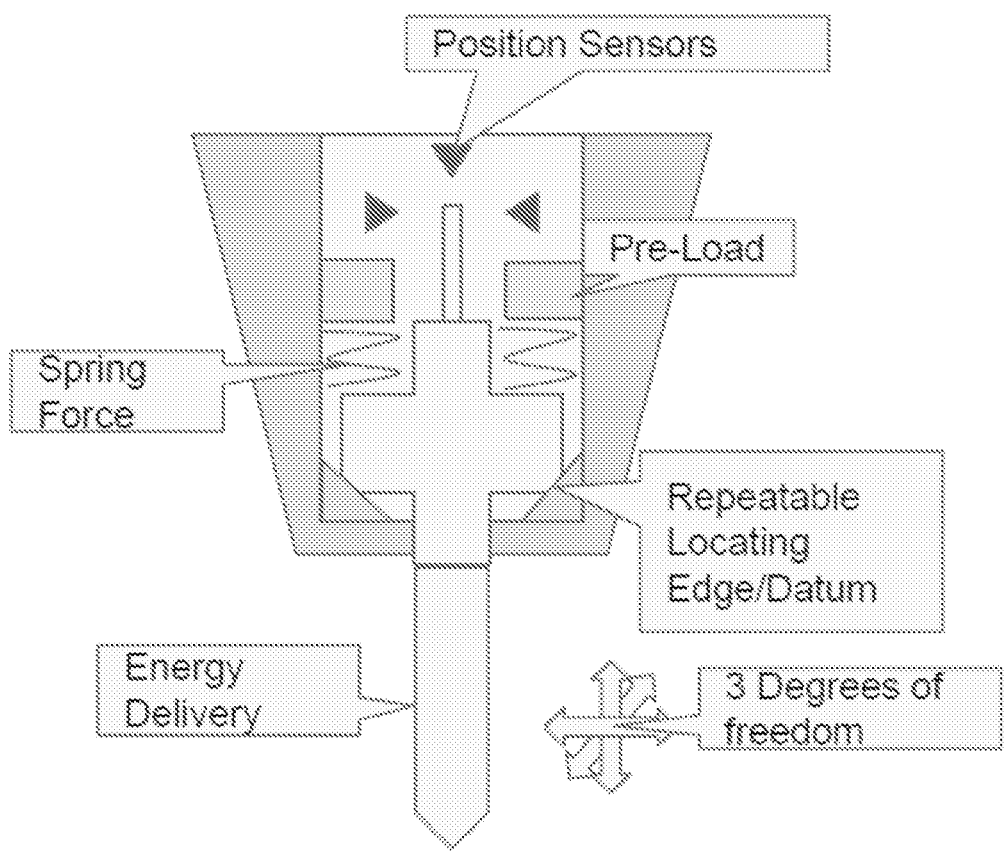
FIG. 9 is a photograph and scheme for components to mount an energy source and determine its position.

The invention features 3D printing technology that bridges the gap between continuous and intermittent processes. This is achieved by utilizing a slurry, which provides the printing medium with physical properties that it would not have in either powder bulk format or solid stock. This slurry allows for the energy delivery system to move freely within it, e.g., submerged or continuously skimming a surface of a fluidized slurry. The slurry will allow for an omnipresent state of printing media to exist whereby printing media will come into contact with the energy source. The energy source can be intelligently switched and moved to a desired location (so called voxel printing), so as to construct a solid object additively by taking the print media out of the slurry and depositing it. Allowing the energy delivery system to be submerged in the slurry opens new possibilities of higher energy efficient processes. Resistive continuous weld pool formation can now take on a 3D object, and likewise laser delivery systems can be submerged, thereby removing the need for focal planes and inefficiencies resulting from scattered light. The fluid in the slurry may provide a desired kinematic viscosity to the printing media. The fluid may also provide process shielding, active or passive filtration, desired ionic states, or all the above during the printing process, allowing for a more homogenous part with repeatable desired properties. Slurries may be chosen to become solid at a desired temperature. The advantage of this is that sensitive or pyrophoric media could be rendered passively inert and can be handled without the need of respiratory/advanced personal protection equipment. Likewise, the media can be safely stored without the risk of contamination to the printing media, reducing the overall risk posed by powders before and after usage. Fluids may be made of materials that could be dissolved by common solvents, such as but not limited to water, allowing for easy cleaning of the final part. The slurry approach allows for unused media to be "pumped" out of the build chamber into a repository so as to reduce the need for post printing material handling drastically. The slurry may thus be kept in a repository within the system and would only need to be "topped" up as the printing media is being consumed by the printing process, ensuring that the printing media is kept at the desired composition and purity when not in use.

In particular, the invention provides devices, systems, and methods for 3D printing. The invention employs slurries of particles or a solute in a carrier fluid, which may be a liquid (e.g., water) or gas, in printing. The use of a slurry is advantageous in allowing for printing in any orientation. Further advantages include the ability to print sub-10 µm powder (including nanoparticles); improved process and final part properties for parts printing with sub-20 µm powder; improved printing speeds at higher levels of detail with no recoating time; process accuracy and final part detail is less limited by print media shape or size, as well as not limited by the particle size distribution within the slurry; safer handling of pyrophoric printing media; no requirement for a shielding gas; improved life cycle uses of the printing media, due to active passivation and shielding provided by the carrier fluid during printing and passive passivation after use; the ability to use room temperature solidification to reduce the demand on storage conditions and containment; ability for use in low gravity applications, as the slurry does not have a dependency on gravity in order to "wet" the area of intended deposition; ability to carry out in situ material thermal processing (such as tempering or annealing); and ability to use a wide range of process temperatures (−100° C. to +2000° C.). Printers of the invention may be used with slurries containing nanoparticle or certain solutes (e.g., solutes for electrochemical deposition) to produce nanoscale features, e.g., nanoprinting.

The invention may be employed in any manner to print 3D objects. In particular, the invention is amenable to orientation independent printing and component repair, e.g., component surfacing (removal or texturing), EDM (electro discharge machining), electropolishing, slurry polishing, laser ablation, and slurry ablation. The invention may be employed to print objects for any suitable purpose, e.g., aerospace, microscale and MEMS devices, and biotechnology (such as scaffolds or components for use with biological materials or objects made from biological materials).

Printers of the invention may be particularly amenable for printing bulk metal glasses (e.g., metals with amorphous atomic scale structure, e.g., metallic glass, e.g., glassy metal).

Printers

Slurries may be employed in printing in a variety of ways. In one aspect the printing occurs at locations submerged in the slurry with suspended particles or a solute. In another aspect, printing occurs at a defined boundary layer between settled particles and the carrier fluid. An exemplary printer is shown schematically in FIG. 1.

Figure 14:
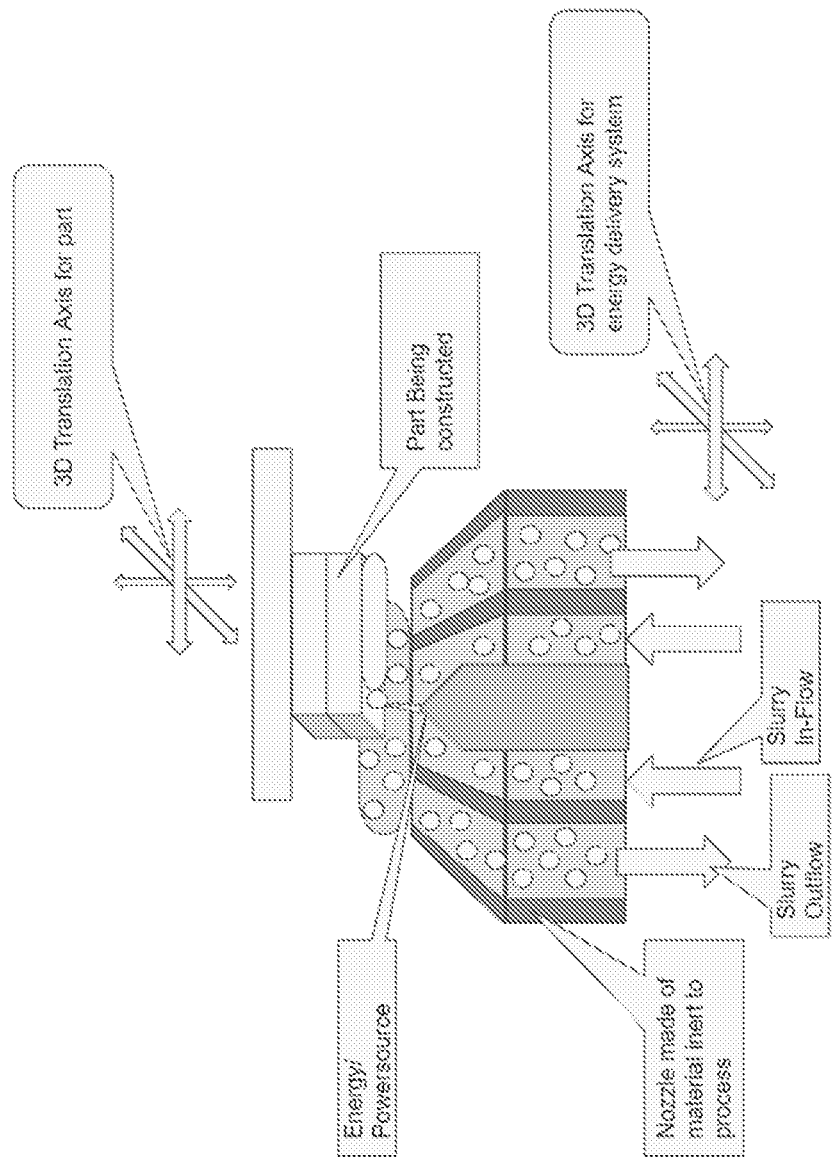
FIG. 14 is a diagram of an energy source including multiple lumens for simultaneous delivery and removal of slurry.
Figure 18:
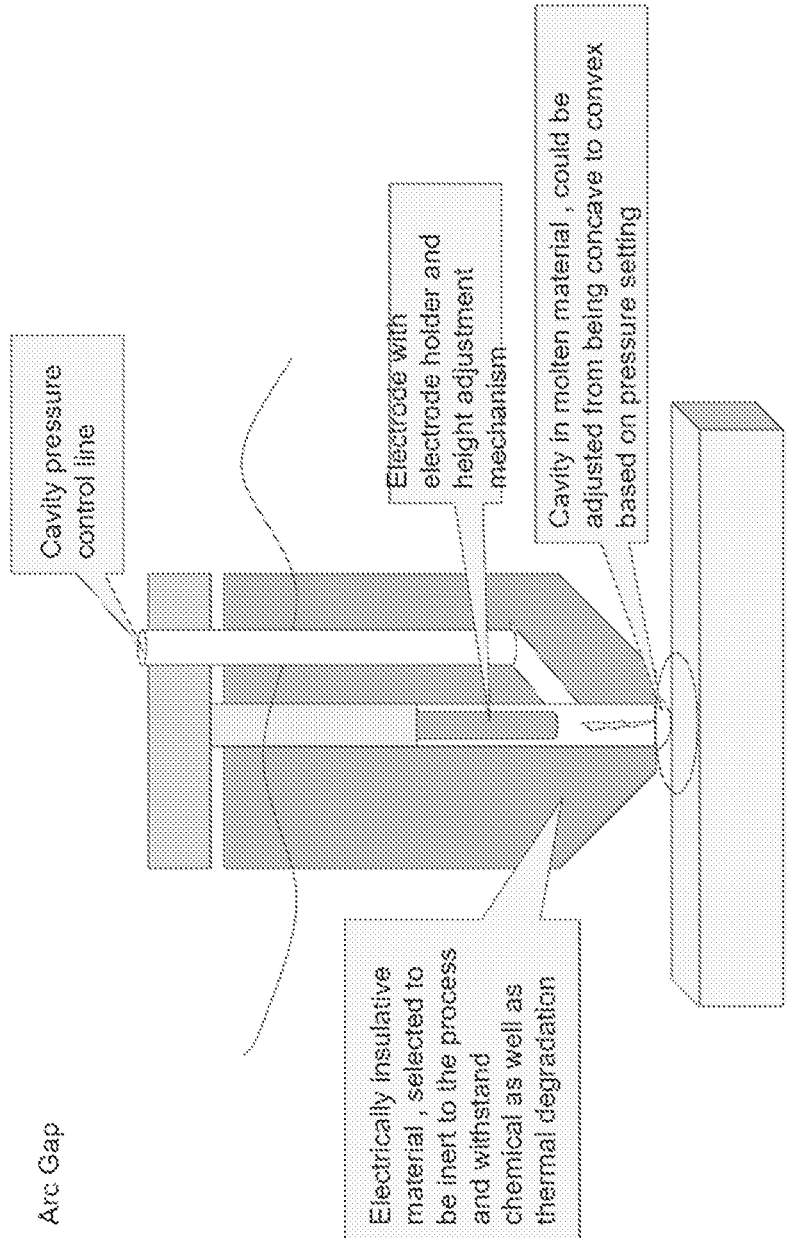
FIG. 18 is a diagram of an electrode energy source including a lumen for supplying a gas flow to the deposition point.
Figure 20:
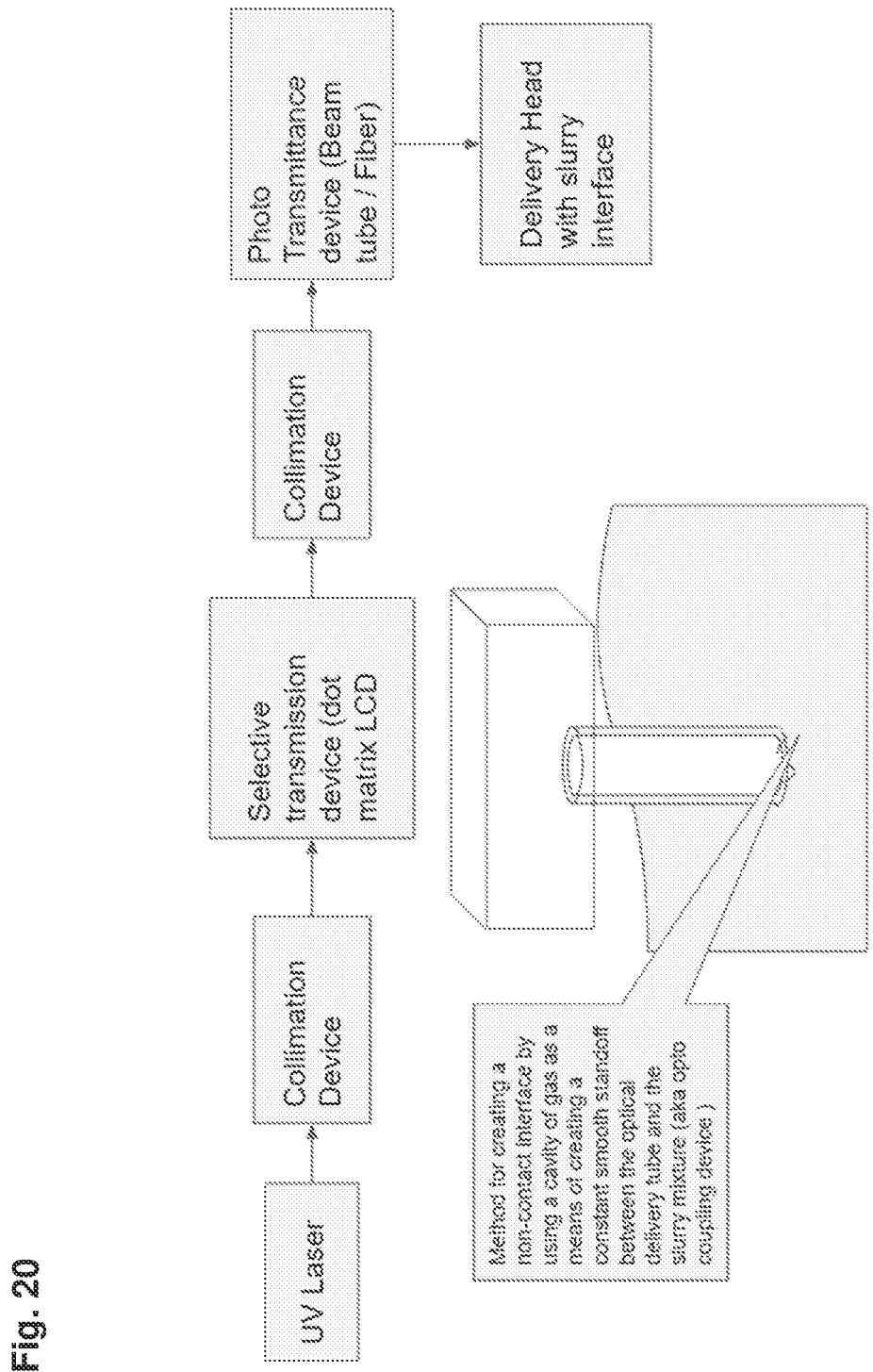
FIG. 20 is a scheme for submerged slurry printing using a UV laser energy source and a gas cavity.
Figure 21:
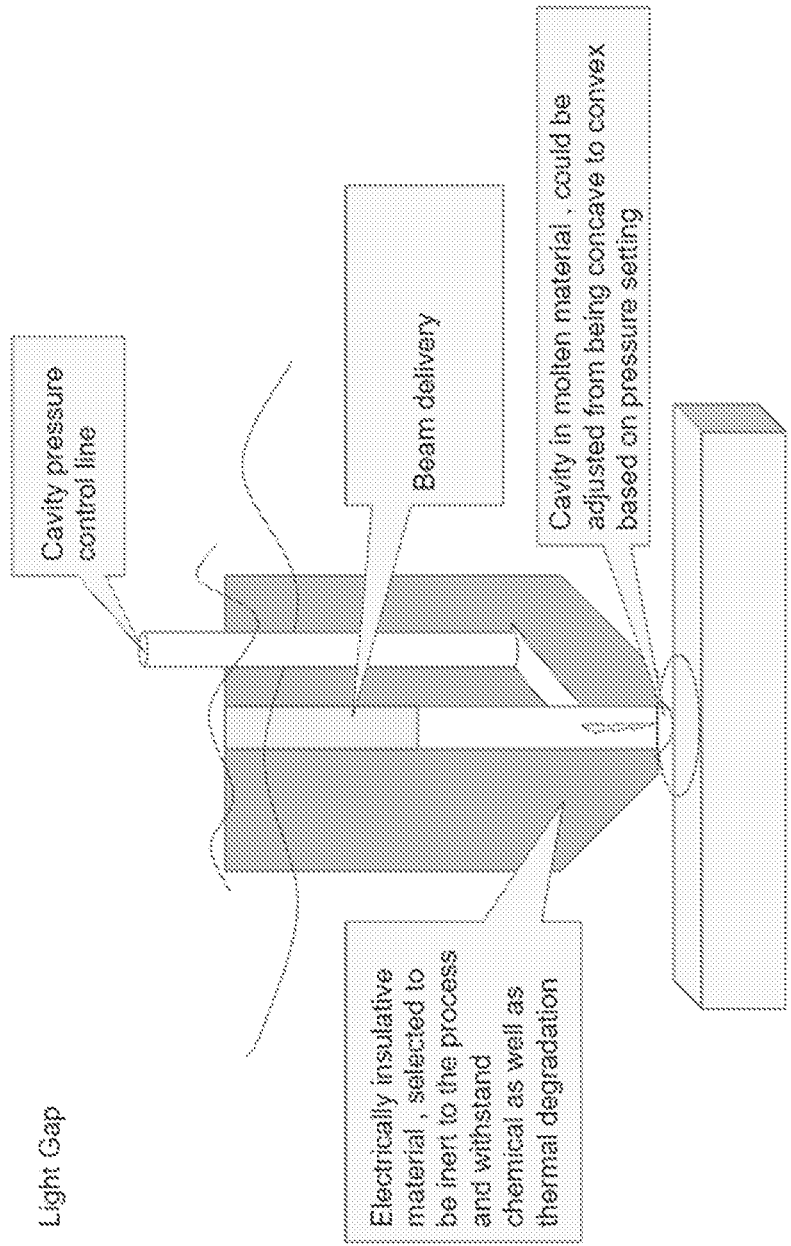
FIG. 21 is a diagram of an optical energy source including a lumen for supplying a gas flow to the deposition point.

The printers will include an energy source that results in deposition of material from the particle or solute in the slurry at a desired position, i.e., creates a voxel at the desired position (FIG. 2). The printer will also include a base, which may be permanently attached, removable or have a removable component attached to a permanent component, on which the object is printed. The object may be attached to the base by cold mounting (FIG. 3), in which localized cooling results in solidification of slurry around the object, holding it in place until heat is added for release. Other methods of attachment include clamps and vices (mechanical or vacuum). The printer can include one or more motion systems, e.g., gantry, to position the energy source and/or base for deposition of voxels. The motion systems may allow for the energy source and/or base to be oriented with the desired degrees of freedom, typically at least two or three, such as x, y, and z or equivalent coordinate system. The motion systems may also provide six degrees of freedom, e.g., x, y, z, roll, pitch, and yaw (or other coordinate system). When both the energy source and base are connected to a motion system, they may have different degrees of freedom that combine to provide the desired motion. The energy source may include a matrix of individually controllable energy sources (e.g., high power LEDs, i.e., where a single LED consumes at least 0.5 W, e.g., 1 W, 2 W, 3 W, 5 W, 8 W, 10 W, 15 W, 18 W or greater, or has an efficiency of between 40 and 683 lm/W, e.g., between 40 and 300 lm/W, between 40 and 100 lm/W, or at least 50 lm/W, 100 lm/W, 200 lm/W, 300 lm/W, 400 lm/W, 500 lm/W, or 600 lm/W), allowing for multiple interactions with the slurry at the same time. The energy source may include one or more light focusing components (e.g., lenses, fiber optics, reflectors, etc.) which concentrate power (e.g., from a matrix of LEDs) at, e.g., a deposition point. An LED energy source may output photonic energy to a region (e.g., the deposition point) in the range of 100 W to 10 KW (e.g., between 100 W and 200 W, between 200 W and 1 KW, between 1 KW and 5 KW, between 5 KW and 10 KW, or at least 1 KW, 2 KW, or 5 KW). Each of the matrix may include one, two, or more degrees of freedom. A slurry may contain two types of material that are deposited by two different wavelengths of light or types of energy, e.g., a curable resin and a metal, and the individually controllable matrix may be used to deposit pure and composite portions in the same substrate. The printer may also employ a mask, e.g., a pixelated dot matrix, e.g., a miniaturized liquid crystal display dot matrix coupled to a UV laser (see, e.g., FIG. 20), through which the slurry is illuminated for deposition. A cavity of gas can be used to provide a gap between the optical energy source and the slurry, e.g., to allow free movement or reduce friction of the energy source within the slurry (see, e.g., FIG. 20). The gas cavity may also be used to shape the slurry in the area of deposition (e.g., to make concave or convex) or displace contaminants that may accumulate. A gas cavity can be used to reduce heat transfer to the surrounding slurry. The printer can also include a build chamber capable of holding the slurry, i.e., being fluid (liquid and/or gas) and/or light tight. The build chamber will include a door or opening to allow removal of the printed object. An opening may be at the top of chamber. A door may be on any face of the chamber, e.g., the top or a side. The door is preferably sealable to prevent leakage of the slurry, e.g., if located on the side. In one embodiment, the build chamber is insulated and has a heat removal device (e.g., heat sink or Peltier) that solidifies the slurry into a plug in an outlet (FIG. 4). By heating the solidified plug, the slurry may be drained at an appropriate time. A motion system may be provided to move the base into or out of the build chamber. Additional components may include inlets and outlets for the slurry. In one aspect, the energy source includes a lumen for delivery of slurry to the site of deposition. The energy source may include multiple lumens for simultaneous delivery and removal of slurry (see, e.g., FIG. 14). The deposition point may be surrounded by an outer shroud that is inert to the printing process conditions. The outer shroud may act to limit the area to which the slurry is applied. Applications for simultaneous delivery and removal can include times where a part is too large to fit in a build chamber. The simultaneous delivery and removal of the slurry may be modulated to leave behind some slurry, e.g., to act as a protective layer or for finishing. The simultaneous delivery and removal of the slurry may be used to rapidly cool a substrate, e.g., to produce substrates including bulk metal glasses. Alternatively or in addition, a lumen may be configured to deliver a gas flow to the deposition point, as shown in FIG. 18 and FIG. 21. Delivering a gas flow can create a gap between the energy source and the slurry and/or substrate. The gap formed by the gas flow may be advantageous for certain energy sources, e.g., optical or electrode energy sources. The gap may also act to reduce friction between the energy source and the substrate and/or slurry (e.g., an air gap). The gas flow may protect the weld pool, e.g., by creating an inert atmosphere around it, or by providing, e.g., thermal, electric, ionic, or capacitive isolation. The gas flow may also act to cool the substrate (e.g., for printing bulk metal glasses). In some embodiments, the gas is provided by vapors produced by the printing process and the lumen is configured to capture a portion of the vapors. Printers may further include reservoirs to store unused or waste slurry and pumps to introduce or remove slurry and/or agitators or mixers to prevent settling of particles. Nozzles and semi permeable boundary diffusers may act as agitators to maintain a homogeneous fluidized state, if needed. The carrier fluid and particles in a slurry may be stored in separate reservoirs and may be mixed prior to or upon introduction into the build chamber. The various components of a printer may be disposed in a housing or framework. The printer may also include environmental controls, e.g., to control the temperature, humidity, and/or pressure in the build chamber or elsewhere in the printer. Printers may further include or be connectable to one or more computers or other controllers to control the deposition process (including energy deposition and relative positioning of the energy source and base or object being printed); introduce, remove, or agitate/mix the slurry; and environmental or other process controls. A connection to a computer may be wired or wireless. Components to clean a finished printed object may also be included, e.g., inlets or jets for rinsing fluid (e.g., water), a tumbler, a blaster (e.g., with fine particles like sand or ceramics), or a source of heat or gas for evaporation.

The printing may be controlled manually, e.g., for repair of objects, or be automated, e.g., by provision of an appropriate computer file. An exemplary process flow is shown in FIG. 5. Printing may be employed to build an object from scratch (FIG. 6) or to repair or add to an existing object (FIG. 7).

The components of a printer may be implemented as a single device or as a system of distinct, but operably connected, devices. Systems may also include the slurry or object being printed.

The reservoir for the slurry would have the ability to store the slurry at a desired temperature, e.g., to solidify or liquify the slurry or to provide the desired viscosity. The reservoir may make use of positive pressure displacement, whereby a gas under pressure is used as a means of pumping the fluid to and from the build chamber, eliminating the need for mechanical interaction with the slurry when pumping. The build chamber and reservoir may be configured so that when slurry is required that positive displacement by means of supplementary gas pressure allows for the slurry to be pumped to the chamber, and by regulation of gas pressure and making use of gravitational force, the slurry can be drained or set to a desired level within the build chamber.

A printer may have more than one energy source, e.g., independently controlled from one another, allowing for higher process speeds and or process detail. Likewise, a printer may make use of multiple energy delivery types at the same time for desired effect.

A slurry filtration device may be used to filter out undesired elements or contaminants from the carrier fluid. This device could be active or passive in nature. Filtration could also be achieved by adding desired additives to the carrier fluid rendering contaminants inert to the process.

Figure 15:
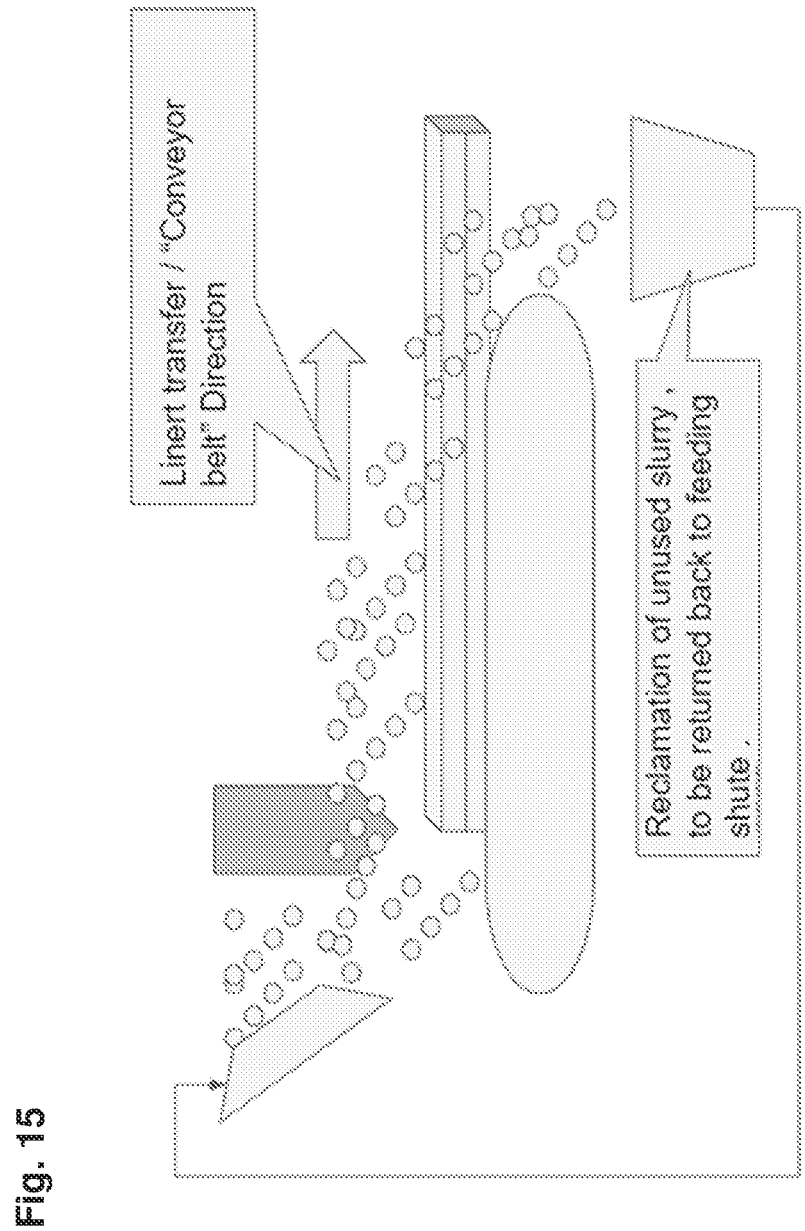
FIG. 15 is a diagram of a printer including a continuously movable base.

A printer may include a continuously movable base (e.g., a conveyor belt or rotating disc) as shown in FIG. 15. A continuously movable base may be used to, e.g., produce substrates or parts of extreme length. Slurry may be provided as a cascade or other kind continuous flow from, e.g., a chute or nozzle. The printer may additionally feature a system to collect and recycle the unused slurry.

Figure 17:
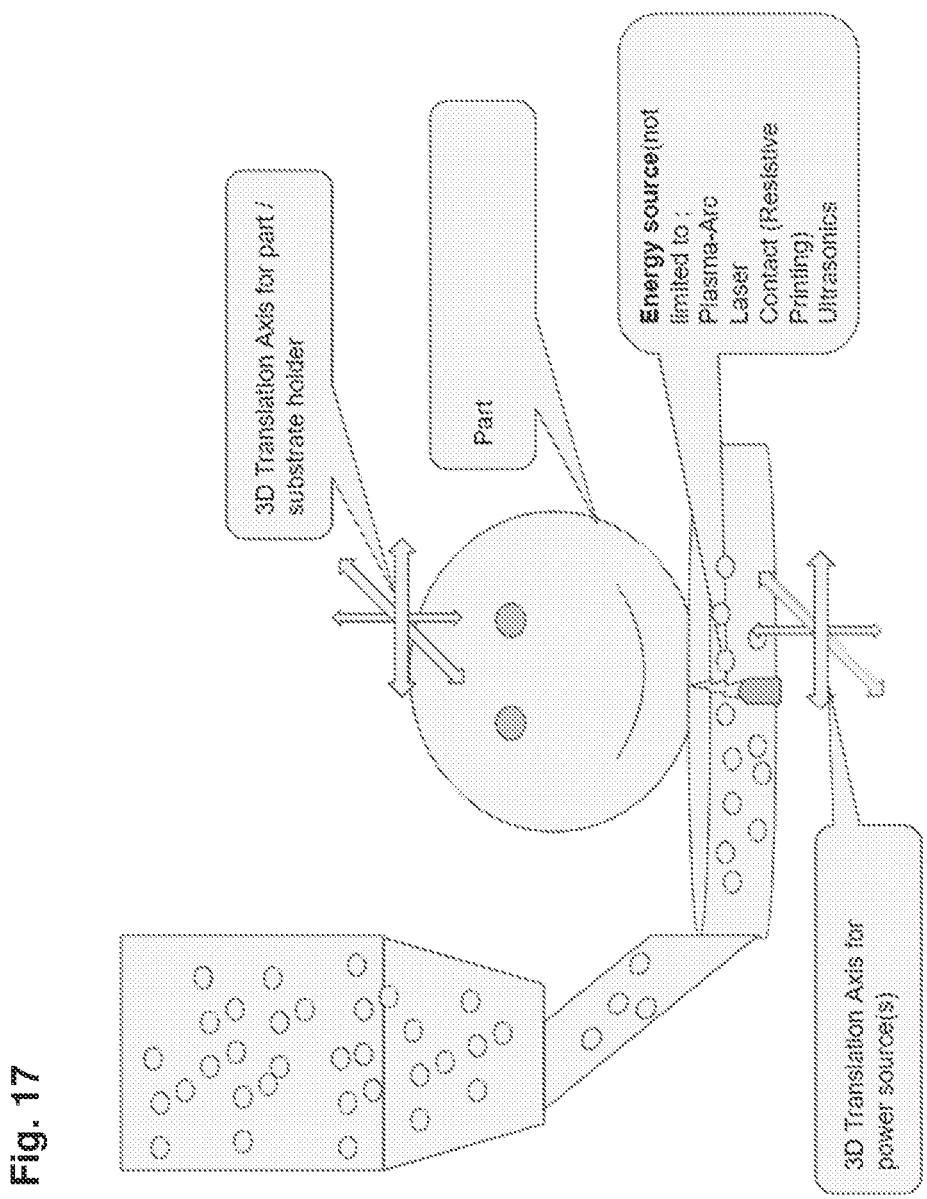
FIG. 17 is a diagram of a printer with a movable bath that includes the energy source.

A printer may include a movable bath that includes the energy source, e.g., to allow a shallow pool of slurry to be used, as shown in FIG. 17. The bath and substrate may be moved independently, and additional layers are deposited as the bath and substrate are moved apart. The bath may include energy sources including a dot-matrix of light sources.

Printers using gas fluidization or using gas for other means (e.g., to create a cavity) may include systems to recover and recycle the gas. Gas recovery and recycling systems may include a gas purification system to remove oxygen and/or water. A gas purification system may include a compressor coupled to a filter containing media that react or otherwise sequester water and oxygen, or other unwanted gases or aerosols.

Printers of the invention may be particularly amenable to direct printing.

Printers of the invention may be particularly amenable for the extraction of minerals from raw materials. For example, where the slurry includes, e.g., regolith or waste mine tailings, various energy sources of the invention (e.g., electrodes, ultrasonic energy sources, direct thermal heating, etc.) may be used to extract (e.g., deposit, e.g., print) metals from, e.g., metal oxide particles in the slurry (e.g., by metal oxide electrolysis). Printers of the invention may be used to directly print an object from such raw materials. Printers of the invention may be used to print in remote environments, e.g., on interplanetary bodies.

Energy Sources

Figure 13:
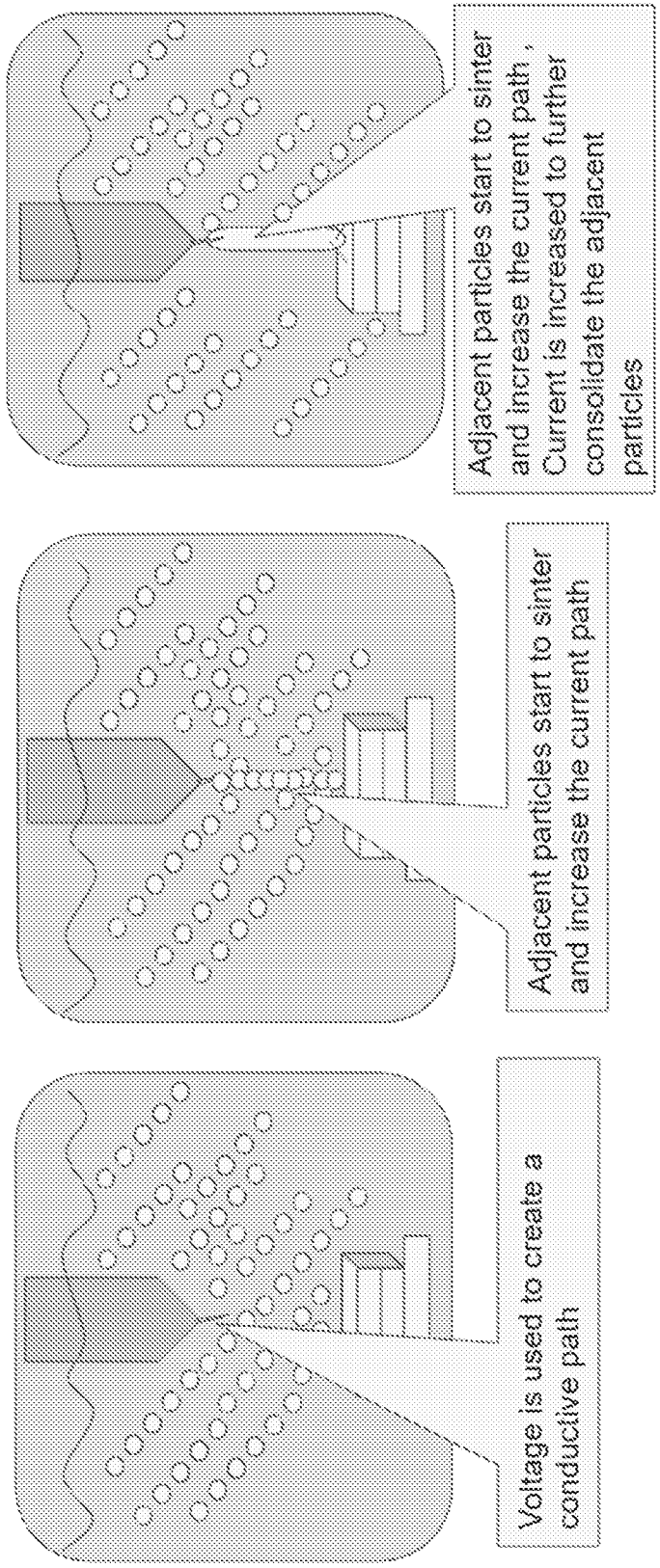
FIG. 13 is a diagram of an arc electrode in a slurry containing conductive particles in a dielectric liquid.
Figure 16:
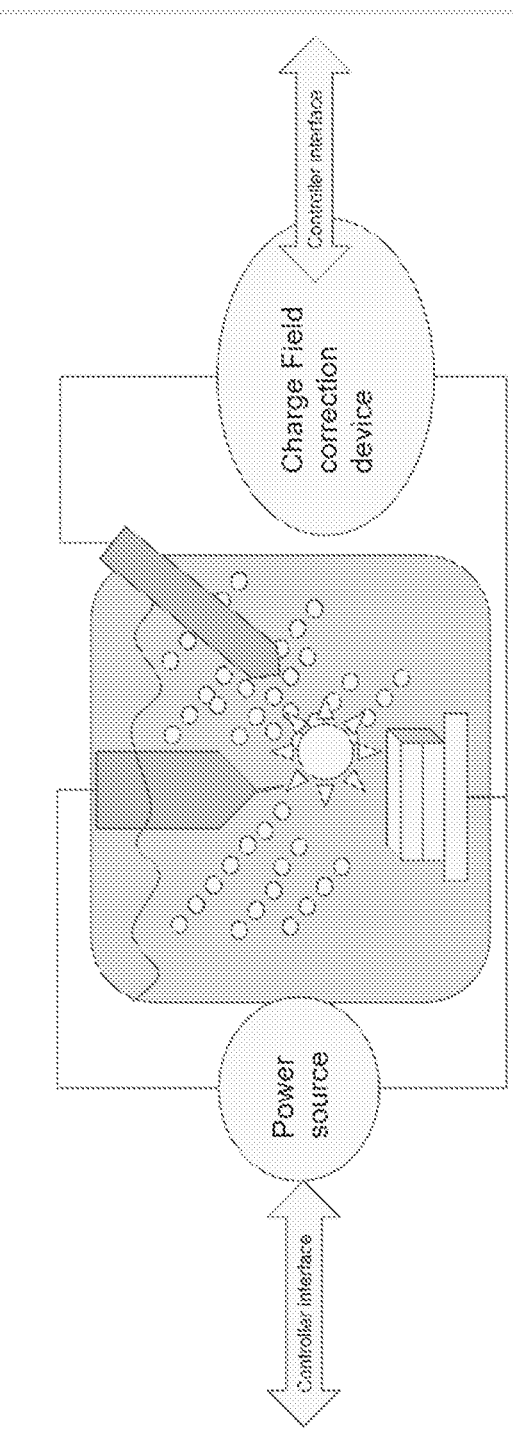
FIG. 16 is a diagram of an energy source including two electrodes.

Any suitable energy source may be employed in a printer of the invention. Examples of energy sources include electrodes (e.g., electrochemical electrodes, e.g., cathode, anode, or AC configurations), single arc electrodes (e.g., cathode, anode, or AC configurations); plasma sources; multiple arc electrodes (e.g., electrode matrix with either cathode, anode, or AC configurations); fissile or radioactive energy source; a particle beam source; a microwave source; a resistive heating source; kinetic energy source; friction sources; single light sources (e.g., UV to far IR spectrum); multiple light sources; RF (Radio Frequency) sources; acoustic or ultrasonic sources (e.g., suitable for welding and/or propulsion); direct heat sources (e.g., a heating element), magnetic energy sources (e.g., induction heaters), and combinations thereof. High power (e.g., having an efficiency of at least 40 lm/W) light emitting diodes (LEDs) may also be used as the energy source. High power LEDs may be directly embedded in the printing head. The energy source may be an ionizing (e.g., a proton, neutron, electron, x-ray source) or non-ionizing (e.g., microwave) radiation source. A radiation energy source may include a shutter that responds to an external stimulus (e.g., heat). An energy source may be a fissile or radioactive energy source. A fissile or radioactive energy source may include a micro fission reactor (e.g., an alpha- or betavoltaic cell, or a miniaturized nuclear fission reactor). A fissile or radioactive energy source (e.g., a micro fission reactor) may provide energy in the form of heat or direct radiation of, e.g., charged particles (e.g., electrons or protons). A fissile or radioactive energy source (e.g., a micro fission reactor) may include a fissile material modulated by control rods within the deposition point of an energy source, e.g., a high heat resistant "pen" which can transfer heat to the slurry. A fissile or radioactive energy source (e.g., a micro fission reactor) may also provide energy to other components of the printer, e.g., to other energy sources or motion systems. In some embodiments, particles, e.g., charged particles, emitted by a fissile material or other source may be directed (e.g., an electron or proton beam), e.g., by magnetic fields, to the slurry, base, or substrate to induce deposition, e.g., by melting. Emitted particles may cause particles or a solute to deposit from the slurry by, e.g., radiolysis (e.g., by initiating a precipitate-forming chemical reaction), agglomeration (e.g., by imparting charge to a particle which attracts other particles), transfer of heat (e.g., kinetic) energy, etc. In resistive heating, particles with electrically conductive properties may heat up and melt due to the current passing through the particles. Alternatively, through resistive heating and direct contact, a weld pool can be created and "pulled" into a desired direction. Switching and controlling the energy source will allow for control and switching of the weld pool. In the event that a nonconductive printing particle is used, a carrier fluid can be used that provides the desired conductivity in the space between the substrate and energy delivery end where either a particle is to be fused or a weld pool is to be created. A kinetic energy source can be used whereby a particulate is physically driven into the substrate by means of a "hammer" action. Alternatively, the kinetic energy can be applied indirectly for example as pressurizing the slurry through a nozzle or accelerating the particulate through means of magnetic force, plasma, or photonic propulsion. A friction source may be employed whereby the gap between the energy delivery system and the substrate can be set such that, when the energy delivery system moves within the slurry, the particulate would grind and interact in such a way that friction forces would melt or deposit the printing media onto the substrate. An electrochemical power source could be used where electric charge is used to create precipitate out of a slurry and selectively deposit this onto a substrate. In some embodiments, the electrochemical power source may induce metal ions, e.g., from the energy source, to electroplate the substrate, e.g., by altering the electric field between the energy source and substrate or the surface charge density of the substrate. Particles and solutes in the slurry may then be deposited on the electroplated layer. Mixture, processes, and materials suitable for deposition by electroplating as described herein are discussed in US20190048486 A1, which are hereby incorporated by reference. In some embodiments, the energy source may feature two electrodes, where a second electrode acts to steer or direct deposition by altering the electric field or current density between a first electrode and the substrate, as shown in FIG. 16. A second electrode may also act as a source or sink of ions to balance the electrochemical reactions of deposition, e.g., a sacrificial anode or cathode. Multiple sacrificial electrodes may be included, e.g., to switch between deposition different ions from solution by switching between electrodes made of different metals. An organic stimuli energy source, such as a hormone/enzyme coated tip that stimulates biological matter in a slurry, allowing the matter to congeal, grow, or deposit out of solution. In some embodiments, the energy source may stimulate biological cell growth by inducing selective scarring or fibrosis of tissue. A catalytic energy source may be employed where a catalyst is selectively exposed to the slurry, allowing for a chemical reaction to occur at the area of exposure resulting in deposition or precipitation of a compound or element. The catalytic interaction could take place near the substrate so as to deposit the intended compound or element onto the substrate. An osmosis energy source may be employed whereby a selectively permeable membrane is used to locally interact with a slurry of a desired composition, leaving a precipitate behind. Where the energy source includes a magnetic energy source, the magnetic energy source may be used to direct particles to the substrate. An arc electrode energy source can be used to create a large gap weld pool by modulating current and voltage when the slurry contains conductive particles (see, e.g., FIG. 13) in a dielectric liquid. The arc electrode may be used initially to gather or align conductive particles to create a conductive path (e.g., less than 1 KΩ at 1 inch separation and about 300 V). By this method, arc welding can be carried out at voltages considerably lower than the voltage required to create a conductive path in air (about 76,000 V), for example, about 300 V. A large gap weld pool may be advantages for producing parts or features of parts that are narrow and or long, e.g., low aspect ratio features.

An energy source may be placed in a tool holder, e.g., with between 2 and 6 degrees of freedom (translation and rotation). Energy sources may also include a lumen for local delivery of the slurry to the point of deposition. The lumen may feature various sizes and shapes of nozzle or may be shapeable. In some embodiments, the nozzle may be shaped during printing, e.g., to create different sized or shaped features on the substrate. The energy source may be multiple energy source that can be switched during printing.

In embodiments, the weld pool can be manipulated by being pulled or pushed by relative movement of the energy source (or probe positionable to contact the weld pool) and the base or object coupled to the base (e.g., the substrate). In these embodiments, the weld pool may be in contact with the output point of the energy source or a probe, e.g., metal rod, that is coupled to the energy source or independently movable. An independently movable probe may be positioned near the output of the energy source so that it is manipulating molten material. In one example, an energy source may include a tip with particular properties (e.g., surface energy, shape, etc.) to optimize surface interaction with a particular weld pool for a particular print. An example of an energy source capable of manipulating a weld pool is shown in FIG. 8. The energy source provides high efficiency laser direct contact delivery. The energy source forms a weld pool by sandwiching a particle slurry between the laser delivery and substrate. Energy is applied, and the weld pool meniscus is allowed to adhere to the optical tube eliminating the need for a focal plane and the issues that come with trying to maintain a fixed focal plane. Energy reflections are maintained in the optical tube and not allowed to reflect off the weld pool, thus improving the efficiency of the laser, e.g., through limiting scattered light. The optical tube and support may be designed to interact with the surface tension of the weld pool, allowing the migration of the weld pool by "pulling" it into a desired direction. Moving into any new direction will cause solidification of some of the weld pool as it interacts with a cold surface, resulting in "necking" of the weld pool. This necking and new gap formation will allow the slurry, with suspended particles to enter the void, allowing more particles to interact with the weld pool, adding to the weld pool mass. The process is repeated in continuous or voxel form, while moving the energy source and switching the laser source, until a desired near net shape is formed. An optical wedge or back reflection system may be utilized to divert any energy not absorbed by the weld pool and in doing so also prevent damage to the laser source. Control and monitoring equipment may be used to ensure that the desired energy is being applied.

The energy source may be coupled to a self-locating feature, e.g., by pneumatic, spring or magnetic coupling (FIG. 9). This feature allows for decoupling and recoupling of the energy source in the situation where the energy source collides with the workpiece or build chamber. This feature will then ensure repeatable positioning once the force applied by the collision is removed. This has the ability to deliberately locate edges in this fashion.

Due to the scalable nature of the technology and the media used, the process allows for low power consumption in the range of 0.1-100 watts, or, for energy intensive process as result of material volumes/properties being processed, power may be in the order of 100 watts to megawatts.

Figure 22:
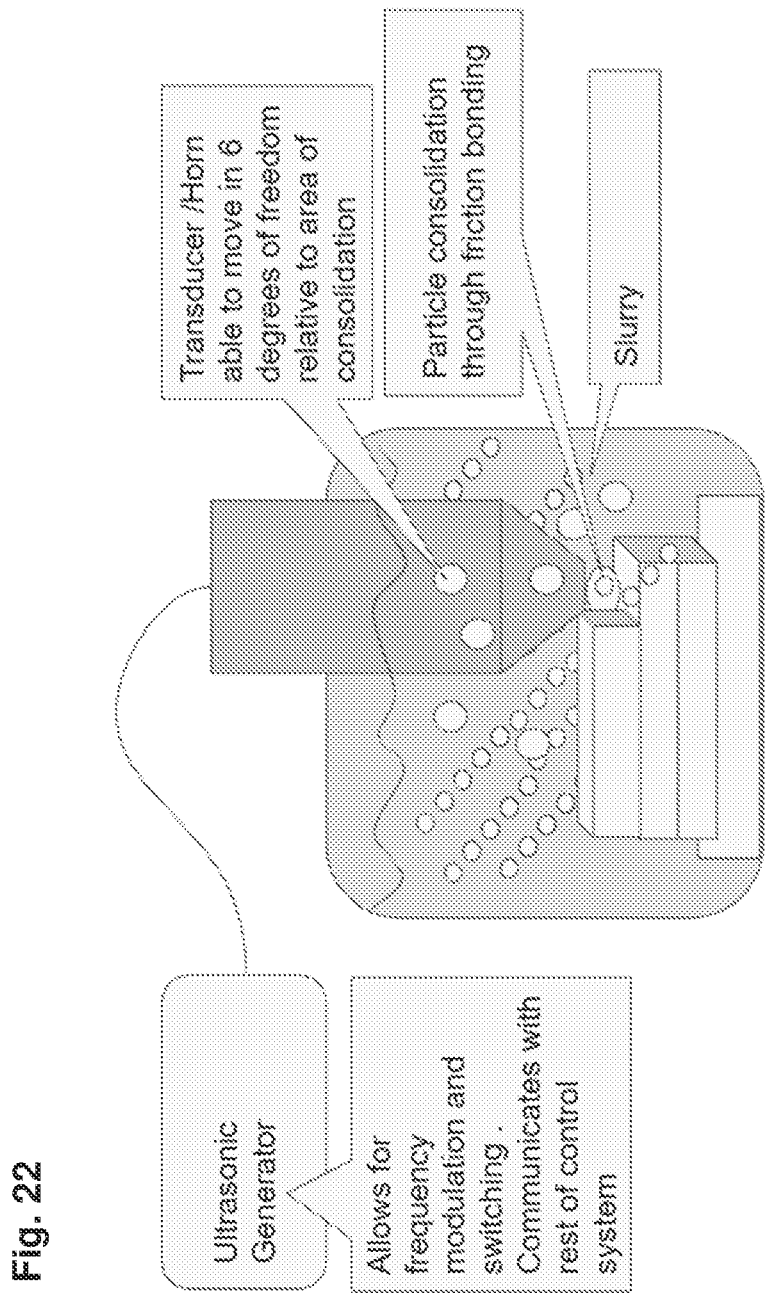
FIG. 22 is a diagram showing an ultrasonic energy source.

Acoustic or ultrasound energy sources may be used to deposit materials (e.g., sources as described in US20180178314). In some embodiments, the acoustic or ultrasonic energy source may include an acoustic resonator which allows the energy source to create and deposit droplets of, e.g., molten metal of specific sizes. Methods and materials suitable for slurry printing using an acoustic or ultrasonic energy source as described herein are discussed in, e.g., Foresti Science advances 4.8 (2018): eaat1659. The omnipresent slurry negates the need to feed material into the deposition area. An acoustic or ultrasonic energy source may include a transducer. A transducer may be used to generate appropriate frequencies and amplitudes of ultrasonic energy for a particular printing application, slurry, or substrate. An ultrasonic energy source may be used to fuse materials below their melting temperature or without heating a large portion of the slurry. An acoustic or ultrasonic energy source may include, e.g., a transducer, a converter, a booster, a sonotrode (e.g., a stack of piezoelectric transducers coupled to a tapering metal rod), etc. An ultrasonic energy source may include a resonator and an acoustic force focusing component (e.g., at the deposition point). Printers and methods of the invention may use resonators and acoustic force focusing components that are smaller than would be operable in laminate-based acoustic or ultrasonic printing systems, allowing higher resolution and lower compression forces. An acoustic or ultrasonic energy source may transfer energy via friction (e.g., FIG. 22). The acoustic force focusing component may be textured, e.g., to increase friction. An acoustic or ultrasonic energy source may include multiple resonators and acoustic force focusing components configured to move independently or in a matrix. An acoustic or ultrasonic energy source may include multiple acoustic force focusing components of variable size and shape which may be switchable during printing, e.g., to print features of different resolution. An acoustic or ultrasonic energy source may direct energy to the slurry in more than one degree of freedom at a time, e.g., two, three, four, five, or six degrees of freedom (see, e.g., FIG. 22). An ultrasonic energy source may be used to de-gas a slurry prior to, or during, printing, e.g., to remove oxygen from an oxygen-sensitive substrate or slurry. Ultrasonic de-gassing may be used during printing using other energy sources. An acoustic or ultrasonic energy source may induce deposition by vibratory compacting, e.g., by driving fluid away from particles and/or fusing them together. Acoustic or ultrasonic energy sources of the invention may be used from printing in microgravity or low gravity environments.

The energy source may also be used to remove particles or a solute deposited during printing, i.e., in situ subtractive printing, e.g., to add detail or fine resolution to a part. Subtractive printing may be achieved using, e.g., discharge machining, milling, and laser milling. After printing, a part may be finished by abrasive and/or electrochemical polishing or surface conditioning in the printer, e.g., by the energy source. Finishing may be achieved in the presence of the slurry, or after draining the slurry. Abrasives may be added to the slurry to aid in abrasive polishing or conditioning. A printer of the invention may include a separate energy source for subtractive printing.

Figure 19:
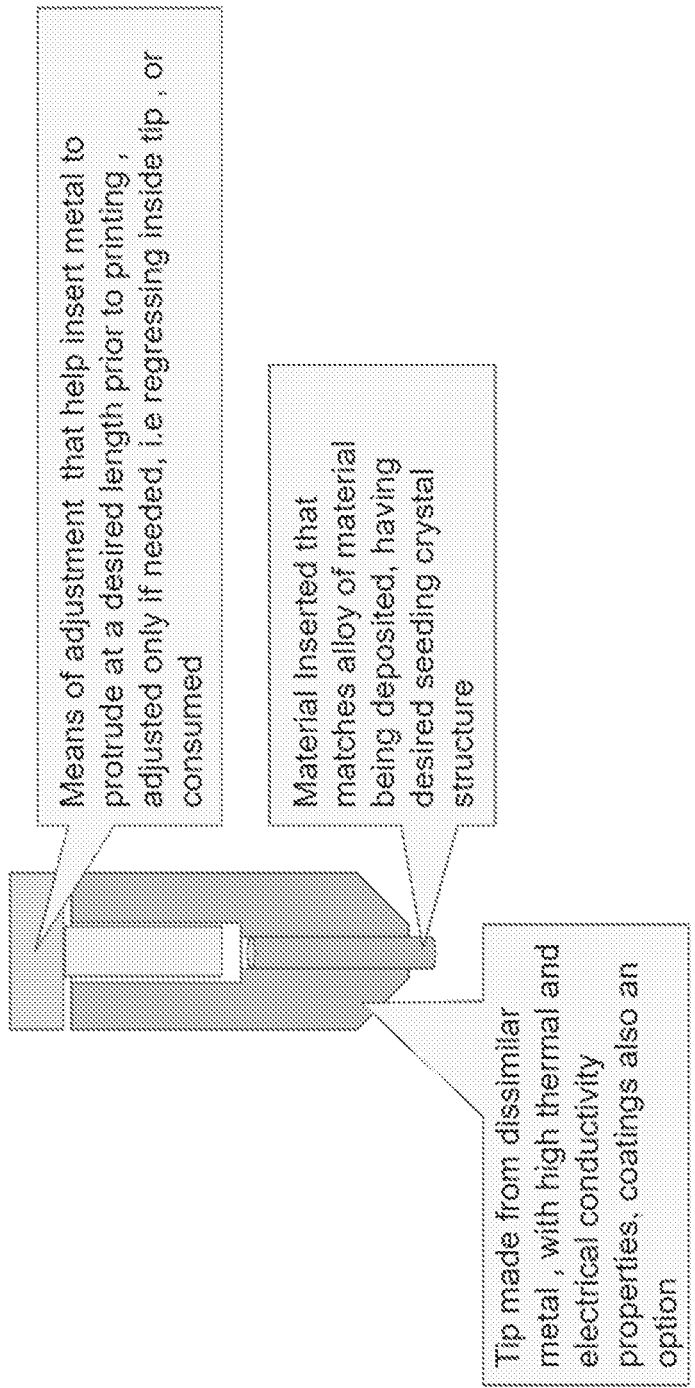
FIG. 19 is a diagram of an energy source including a seeding sample.

An energy source may include a deposition point containing a seeding sample, e.g., a seed crystal, or alloy matching the alloy to be printed (see, e.g., FIG. 19). Including a seeding sample may promote favorable materials properties in the deposited material (e.g., melting point, hardness, etc.), or improve properties of the printing process (e.g., deposition rate, or temperature). A seeding sample, e.g., a monolithic seed crystal may, e.g., afford a desired crystal structure in the part. Alternatively, the energy source may include a deposition point containing a material that is dissimilar to the slurry and/or substrate. The dissimilar material may be an electrode, or a cover or shroud around the energy source.

The dissimilar material may have, e.g., different electrical, electrochemical, or thermal properties. A dissimilar material may be favorable for, e.g., localization of deposited material, or weld pool shaping.

Energy sources amenable to low temperature fusion of materials (e.g., acoustic or ultrasonic energy sources, electrodes, etc.) may be particularly amenable for printing bulk metal glasses.

Slurries

Particles or a solute in the slurry may include any printable material, e.g., metals, polymers, and other compounds. The present invention also allows the printing of other materials to an object, e.g., explosives or isotopes. Materials may be macroparticles (dimensions greater than 1 mm), microparticles (dimensions between 1 mm and 1 μm), or nanoparticles (dimensions below 1 μm). Such materials may also be dissolved in the carrier fluid, e.g., to remain in an ionic state until taken out of solution through electrochemical interaction or perturbed out of solution by an applicable energy source. Examples include titanium, titanium alloys, aluminum, aluminum alloys, steel/stainless steel, nickel, nickel alloys (e.g., inconel or Mar-M), platinum, polymers, and glasses. Cells and other biological materials, e.g., proteins, polypeptides, carbohydrates, or polynucleotides, may also be used as the printing medium. The amount of particles or solute in the slurry is a function of the desired characteristics. The slurry may include any 3D printing ink known in the art. A 3D printing ink may include a mixture of dissolved or suspended solutes or particles disposed to come out of suspension or solution (e.g., change ionic state) in response to stimuli from the energy source to produce a discrete deposit. Particles or a solute may include bulk metal glass alloys (e.g., Zr—Al—Ni—Cu, $Ti_{40}Cu_{36}Pd_{14}Zr_{10}$, or $Mg_{60}Zn_{35}Ca_5$) or precursors for their formation.

The carrier fluid may be liquid or gas and may have a density and/or viscosity to allow suspension or settling of particles as desired. Examples of carrier fluids include molten salts (such as magnesium chloride, lithium chloride, potassium fluoride), molten metals, pressurized gas (e.g., argon, helium, or nitrogen), silicone or mineral oil, polymers, organic solvents, ionic liquids, or inorganic solvents (e.g., water). When the carrier fluid is water, it may be with or without ionic species (e.g., dissolved acid or base, organic or inorganic salts, etc.). When the water contains ionic species, the ionic species may be selected to afford a particular ionic balance (e.g., a particular pH, ionic strength, conductivity, etc.). The carrier fluid may be deionized water. The carrier fluid may be deionized water containing non-ionic solutes. Biocompatible fluids that support or promote cell growth can be used as a carrier fluid. The carrier fluid may also act as a process shielding mechanism and/or process purification mechanism. Carrier fluids may be cooled to allow for rapid cooling of the substrate, e.g., to produce substrates including bulk metal glasses. Carrier fluids for rapid cooling may be cryogenic or have high thermal conductivity. Carrier fluids may include additives to allow them to be further cooled (e.g., glycol).

Additives may be added to the carrier fluid to provide a slurry with desired electrical and/or thermal conductivity, desired kinematic viscosity, and desired melting mechanics, e.g., speed of sound effects or weld pool viscosity/stability. Additives may also create desired cavitation or suppress cavitation in the carrier fluid. In some embodiments, the slurry contains both particles and solutes, and the solutes are deposited by the energy source. For example, a slurry can contain a curable resin and a particulate material that is insoluble in the resin, e.g., titanium powder in a UV-curable resin. A slurry may include a precursor disposed to precipitate in response to a first stimulus from the energy source, creating particles in suspension, which can then be deposited in response to a second stimulus. Additives (e.g., dopants or catalysts) may be provided to the slurry during deposition to alter the thermodynamics of the deposition process at a desired point in the printing, e.g., adding transition metal catalysts (e.g., platinum, palladium, nickel, etc.). Another example may involve using additives that react together exothermically (e.g., oxide/nitride formations) to provide additional thermal energy to the surrounding slurry.

A slurry may include mixtures that contain dissimilar consolidation materials from other complex mixtures, that allow the consolidation of a desired slurry at a desired location. In some embodiments, consolidation may result in the deliberate entrapment of a first mixture in a consolidated matrix (e.g., a deposited solid or a precipitate) made of different material/or different mixture of materials. Slurries including mixtures containing different materials may be used to produce self-healing materials, e.g., where the healing material(s) (e.g., materials that react to change composition in response to an external stimuli) are encapsulated in a parent material in a different state. In embodiments for bio printing, consolidated slurries including, e.g., hydrogels, scaffolding materials, and cells may be formed. The cells being entrapped in a matrix of scaffolding materials during printing. Other embodiments include, but are not limited to, ceramics or metals trapped in resins or binding agents, or the reverse. During submerged slurry printing of the slurries including a mixture and a binding agent, the binding agent hardens or comes out of suspension/solution by selective deposition using an energy source specific to the binding agent. Depending on the application, the resin or binding agent could be left in place or undergo post processing to remove the binding agent, e.g., as in the case of green parts made during binder jet printing. A slurry may be a liquid-like solid emulsion, e.g., an emulsion glass (see, e.g., Hu, Ssu-Wei, et al., ACS Appl. Mater. Interfaces 2020, 12, 21, 24450-24457).

A stirring paddle or turbine may be used to test the consistency of the slurry by means of viscosity resistance. Other industrial standard methods exist and may be implemented to measure the slurry consistency, e.g., to indicate when it is suitable for use. A stirring device may also ensure desired mixing of the slurry should it be needed.

Slurries may include raw materials or waste products of industry, e.g., regolith, interplanetary dust, mining waste, slag, mineral deposits, waste mine tailings, etc.

Submerged Slurry Printing

Figure 10:
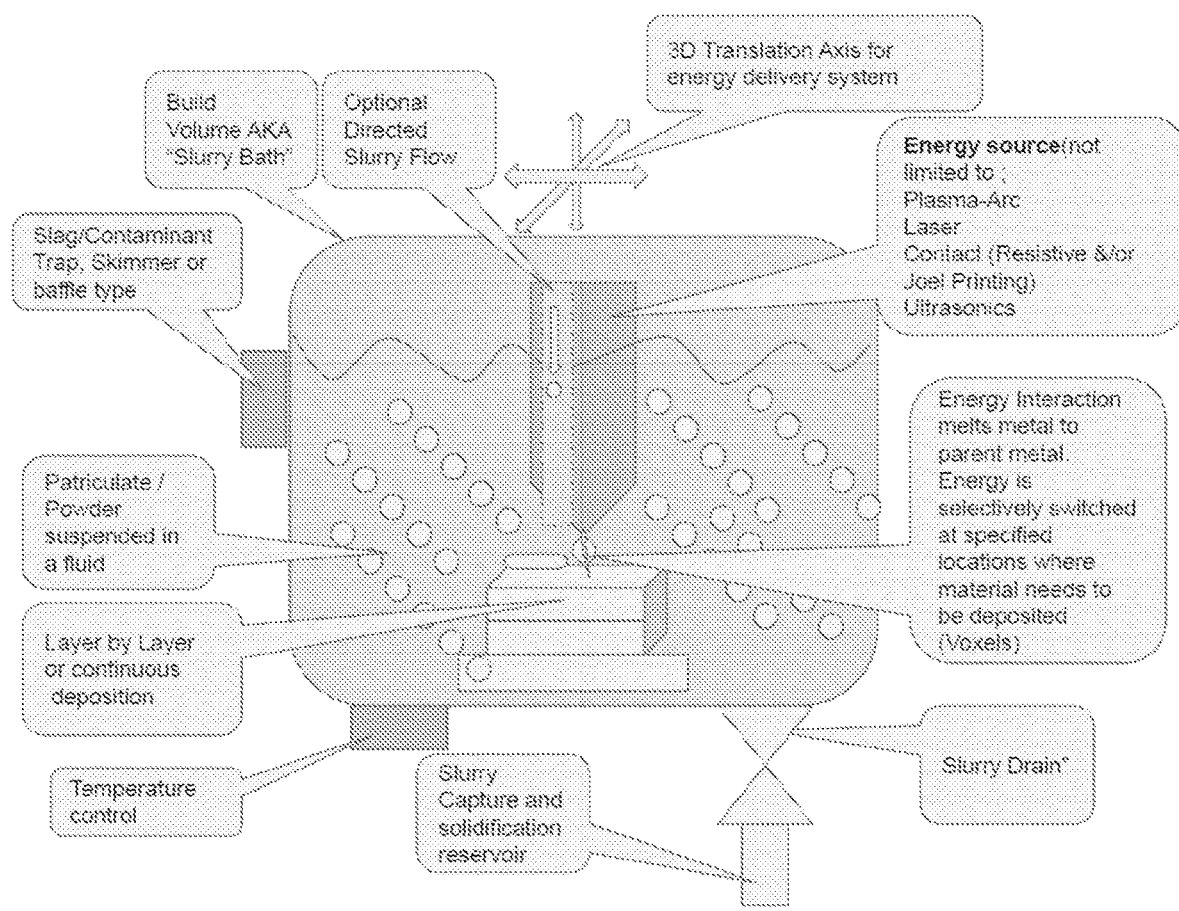
FIG. 10 is a scheme for submerged slurry printing using a liquid carrier fluid.

In submerged slurry printing, voxels of material are selectively added to an object (FIG. 10). Particles or a solute are delivered to the area of intended deposition by a ubiquitous slurry. The energy source moves in the slurry and can be oriented in any required orientation (either alone or in combination with movement of the base). In this embodiment, printing may occur on any face of the object.

Figure 11:
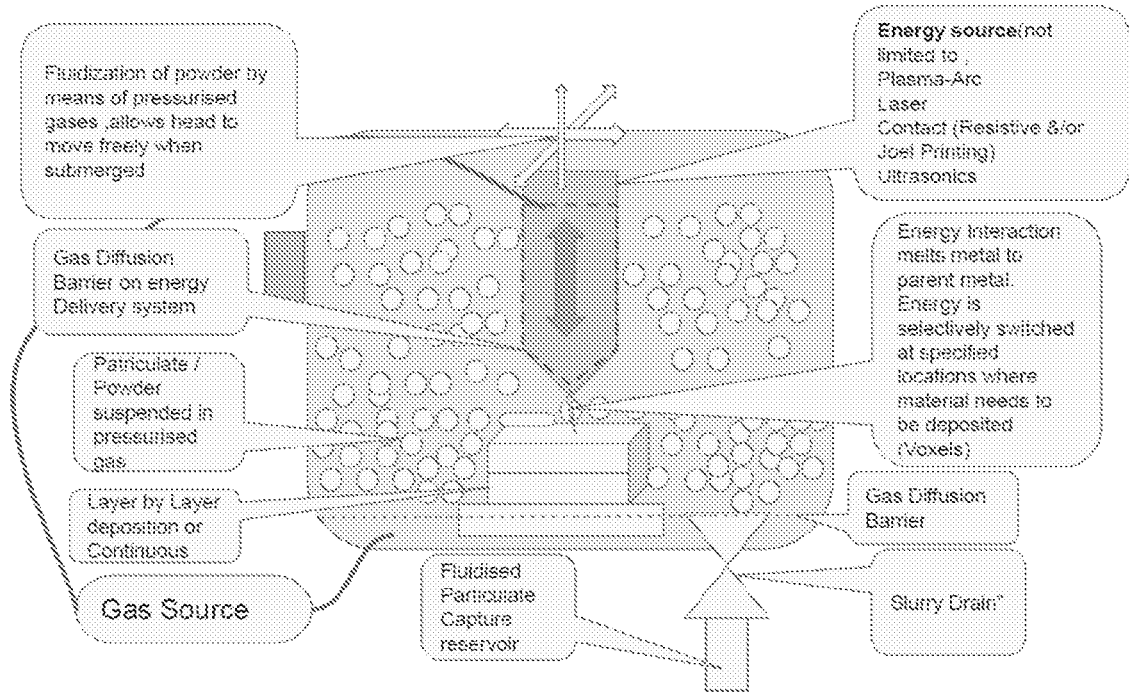
FIG. 11 is a scheme for submerged slurry printing using a gas liquid carrier.

In another embodiment, pressurized gas is used to fluidize a bulk medium containing particles (FIG. 11). In the absence of the gas, the bulk medium would prohibit the free movement of the energy source in the bulk. Use of pressurized gas allows for free motion between particles allowing the bulk mass to act as a fluid, in which the energy source can be moved. An advantage of this process is that it allows for continuous printing, where conventional processes can only be performed in a layer by layer method. This process thus combines a level of detail provided by powder bed or selective laser sintering with the speed of direct energy deposition 3D printing methods. In another embodiment that can be applied to submerged slurry printing, the slurry can contain glass particles and a UV-curable resin (see, e.g., FIG. 20). The pressurized gas may be chilled to allow for rapid cooling of the printed substrate (e.g., to produce substrates including bulk metal glasses).

Slurry Printing at a Boundary Layer

Figure 12:
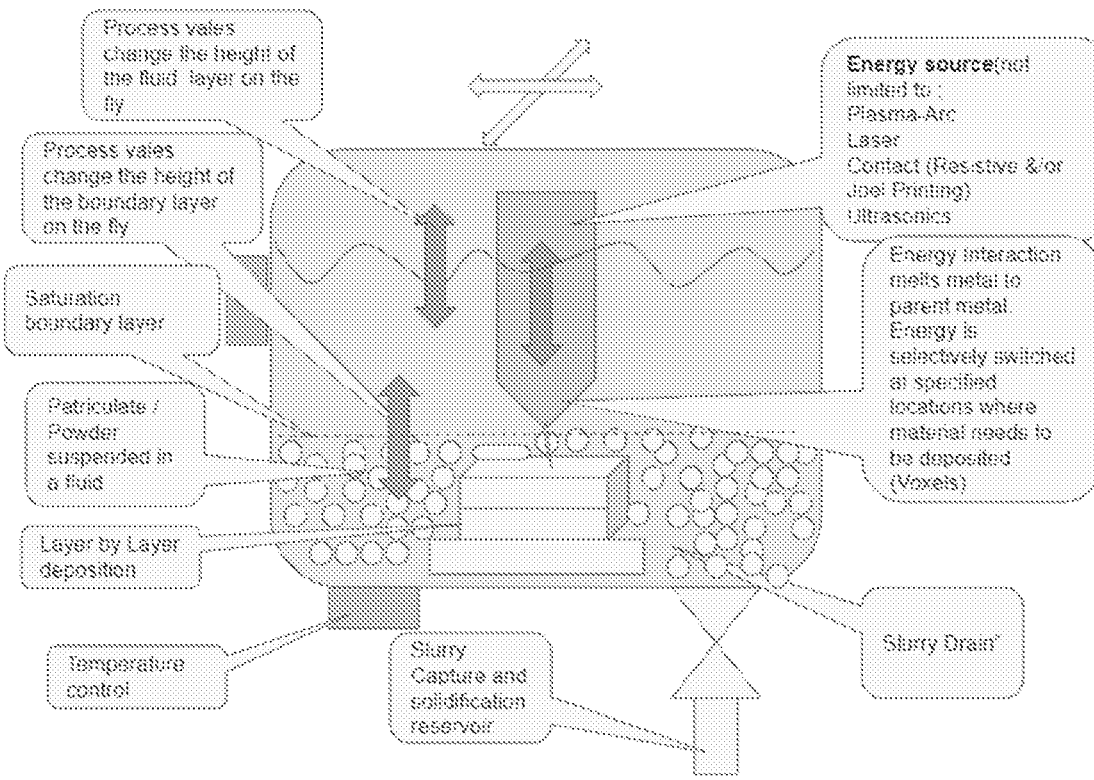
FIG. 12 is a scheme for printing at the boundary of settled particles.

In this embodiment, particles in the slurry settle and form a defined boundary (FIG. 12). Conventional powder bed fusion systems require a leveling device, which is prone to failure, and does not provide fully repeatable results. In this embodiment, the object is created by adding one layer at a time and selectively fusing the particles to the consolidated mass to form a 3D object.

A profound advantage of using a slurry is that the process is in situ able to self-level and repair defects in the boundary separation layer. The boundary separation layer can be tuned during use so that the process has the desired layer thickness, allowing much faster print times than a conventional 3D powder bed fusion system. Another advantage is reduced energy interaction pressure waves, which disturb a powder layer due to rapid gas expansion at the energy interface, whereas in a slurry there is no gas, mitigating this process flaw.

The invention also allows for true hollow and sealed structures to be formed while having the walls of the objects made to any desired thickness. This outcome is achieved by printing an object with an inverted concave void, lowering both the fluid and boundary level, i.e. temporarily draining the slurry, draining any material from this void. Once the material has been drained, the slurry will be reintroduced to the level of the opening, allowing the energy delivery system to "cap" the void and leaving nothing but air (or another fluid, e.g., another gas) in the enclosed space. This method of printing is not possible in most 3D printing technologies, as special design consideration needs to be taken so as to ensure enclosed voids could be drained of powders or support structures.

In some embodiments, a part produced by any device, system or method of the invention may be made partially sintered, e.g., by modulating the energy source to limit fusion between adjacent particles. After draining the slurry, a partially sintered part may be sintered by any means known in the art to increase its theoretical density.

Other embodiments are in the claims.

The invention claimed is:

1. A device for printing comprising:
a) a build chamber capable of holding a slurry;
b) an energy source; and
c) a base,
wherein the energy source is coupled to a motion system to allow relative movement between the energy source and the base; wherein during a printing process the energy source is configured to be submerged within the slurry and positioned at a desired location away from the base or an object coupled to the base; wherein the motion system allows for the energy source to be oriented with at least 3 degrees of freedom; wherein during the printing process the energy source is configured to form in a large gap a weld pool or sintered particles from particles in the slurry; and wherein during the printing process the motion system allows for relative movement of the energy source or base to shape the weld pool or sintered particles.

2. The device of claim 1, wherein the energy source comprises an electrode; a plasma source; a resistive heating source; a light source; an ultrasonic source; or a combination thereof.

3. The device of claim 2, wherein the light source comprises a UV light and/or one or more LEDs, wherein each of the one or more LEDs has an efficiency of at least 40 lm/W; or
wherein the electrode comprises an arc electrode.

4. The device of claim 1, wherein the slurry comprises a carrier fluid that is a liquid or gas; or
wherein the slurry comprises a liquid-like solid emulsion.

5. The device of claim 1, further comprising a reservoir for storing the slurry outside of the build chamber;
an agitator or mixer operably connected to the build chamber;
a temperature, pressure, or humidity controller operably connected to the build chamber; or one or more additional energy sources, wherein the energy source and the one or more additional energy sources are configured to be switched with each other during the printing process.

6. The device of claim 1, (i) wherein the energy source comprises a deposition point and a lumen disposed to deliver the slurry to the deposition point;
(ii) wherein the energy source comprises a laser and an optical tube, wherein light from the laser exits via the optical tube and melts the particles in the slurry to provide in the large gap the weld pool; or
(iii) wherein the slurry comprises conductive particles in a dielectric liquid.

7. The device of claim 6,
wherein for (i) the lumen is configured to be re-sizeable or replaceable during the printing process.

8. The device of claim 1, wherein the build chamber comprises a movable bath for the slurry and the energy source, wherein the base is held above the bath, and the bath and base are movable relative to each other.

9. A method for printing comprising:
a) providing a device according to claim 1, and the slurry comprising the particles disposed in the build chamber so that the energy source is located in the slurry;
b) positioning the energy source relative to the base or the object coupled to the base at the desired location in the build chamber; and c) actuating the energy source to form in the large gap the weld pool or sintered particles that is/are shaped on the base or the object coupled to the base to produce a printed object.

10. The method of claim 9, wherein the particles are evenly suspended in the slurry;
wherein the slurry contains particles that settle within the slurry to create a boundary layer within the slurry;
wherein the slurry comprises a liquid-like solid emulsion;
wherein the particles comprise metal, polymer, or glass;
wherein the slurry comprises mineral ore, interplanetary dust, regolith, mining tailings, and/or slag;
wherein the slurry comprises two or more materials that fuse; or
wherein the slurry comprises conductive particles in a dielectric liquid.

11. The method of claim 1, wherein actuating the energy source in step (c) occurs at a voltage insufficient for breakdown of the dielectric liquid in the absence of the conductive particles.

12. The method of claim 9, wherein the energy source comprises an electrode; a plasma source; a resistive heating source; a light source; an ultrasonic source; or a combination thereof.

13. The method of claim 12, wherein the light source comprises a UV light and/or one or more LEDs, wherein each of the one or more LEDs has an efficiency of at least 40 lm/W; or
wherein the electrode comprises an arc electrode.

14. The method of claim 9, (i) wherein the energy source comprises a deposition point and a lumen disposed to deliver the slurry to the deposition point;
(ii) wherein the energy source comprises a laser and an optical tube, wherein light from the laser exits via the optical tube and melts the particles in the slurry to provide in the large gap the weld pool; or
(iii) wherein the slurry comprises conductive particles in a dielectric liquid.

15. The method of claim 14,
wherein for (i) the lumen is re-sizeable or replaceable during the printing process;
wherein for (i) the energy source can be switched with an additional energy source during the printing process.

16. The method of claim 9, further comprising:
d) removing the slurry from the build chamber; and
e) sintering the printed object or using the energy source or a second energy source to remove deposited particles from the printed object; or
d) polishing the printed object.

17. The method of claim 16, wherein the polishing comprises adding an abrasive to the slurry or using the energy source.

18. The method of claim 9, wherein
step (c) comprises providing additives to the slurry during deposition;
in step (c) the energy source causes particles to melt or sinter by resistive heating; or
wherein step (c) comprises melting particles in the slurry with the energy source to form in the large gap the weld pool and manipulating the weld pool.

* * * * *

UNITED STATES PATENT AND TRADEMARK OFFICE
CERTIFICATE OF CORRECTION

Page 1 of 1

PATENT NO. : 12,172,373 B2
APPLICATION NO. : 17/292313
DATED : December 24, 2024
INVENTOR(S) : Steven Lubbe It is certified that error appears in the above-identified patent and that said Letters Patent is hereby corrected as shown below:

In the Claims

Column 18, Claim 3, Line 29, replace "40 Im/W" with --40 lm/W--.

Column 19, Claim 11, Line 16, replace "The method of claim 1" with --The method of claim 10--.

Column 19, Claim 13, Line 27, replace "40 Im/W" with --40 lm/W--.

Signed and Sealed this
Thirteenth Day of May, 2025

Coke Morgan Stewart
*Acting Director of the United States Patent and Trademark Office*